(12) United States Patent
Tashiro et al.

(10) Patent No.: US 8,853,173 B2
(45) Date of Patent: Oct. 7, 2014

(54) SYNTHETIC GLYCOLIPID AND USE THEREOF

(75) Inventors: Takuya Tashiro, Kanagawa (JP); Kenji Mori, Kanagawa (JP); Masao Shiozaki, Kanagawa (JP); Masaru Taniguchi, Kanagawa (JP); Hiroshi Watarai, Kanagawa (JP)

(73) Assignee: RIKEN, Wako (JP)

( * ) Notice: Subject to any disclaimer, the term of this patent is extended or adjusted under 35 U.S.C. 154(b) by 92 days.

(21) Appl. No.: 13/577,159

(22) PCT Filed: Feb. 4, 2011

(86) PCT No.: PCT/JP2011/052415
§ 371 (c)(1),
(2), (4) Date: Sep. 19, 2012

(87) PCT Pub. No.: WO2011/096536
PCT Pub. Date: Aug. 11, 2011

(65) Prior Publication Data
US 2013/0005669 A1    Jan. 3, 2013

(30) Foreign Application Priority Data
Feb. 5, 2010 (JP) ................. 2010-024859

(51) Int. Cl.
C07H 17/02 (2006.01)
A61K 31/7028 (2006.01)
A61P 31/04 (2006.01)
A61K 31/7032 (2006.01)
C07H 15/04 (2006.01)

(52) U.S. Cl.
CPC ............ *C07H 15/04* (2013.01); *A61K 31/7032* (2013.01)
USPC ........................................ 514/25

(58) Field of Classification Search
None
See application file for complete search history.

(56) References Cited

U.S. PATENT DOCUMENTS

| | | | |
|---|---|---|---|
| 6,531,453 B1 | 3/2003 | Taniguchi et al. | |
| 6,747,010 B2 * | 6/2004 | Taniguchi et al. | 514/25 |
| 8,163,705 B2 * | 4/2012 | Tashiro et al. | 514/25 |
| 8,173,608 B2 * | 5/2012 | Fuhshuku et al. | 514/27 |
| 8,580,751 B2 * | 11/2013 | Shiozaki et al. | 514/25 |
| 2003/0139351 A1 | 7/2003 | Taniguchi et al. | |
| 2006/0269524 A1 | 11/2006 | Kumazawa et al. | |
| 2009/0048185 A1 | 2/2009 | Miyake et al. | |
| 2009/0221516 A1 | 9/2009 | Tashiro et al. | |
| 2011/0104188 A1 | 5/2011 | Tashiro et al. | |

FOREIGN PATENT DOCUMENTS

| | | |
|---|---|---|
| JP | 01-093562 A | 4/1989 |
| JP | 2004-131481 A | 4/2004 |
| JP | 2005-263797 A | 9/2005 |
| WO | WO 98/44928 A1 | 10/1998 |
| WO | WO 03/105769 A2 | 12/2003 |
| WO | WO 2007/049819 A1 | 5/2007 |
| WO | WO 2007/099999 A1 | 9/2007 |
| WO | WO 2008/082156 A1 | 7/2008 |
| WO | WO 2009/119692 A1 | 10/2009 |

OTHER PUBLICATIONS

Borg et al., *Nature*, 448: 44-49 (2007).
Burdin et al., *The Journal of Immunology*, 161: 3271-3281 (1998).
Cui et al., *Science*, 278: 1623-1626 (1997).
Karlsson et al., *Biochimica et Biophysica Acta*, 316: 317-335 (1973).
Kawano et al., *Proc. Natl. Acad. Sci. USA*, 95: 5690-5693 (1998).
Kawano et al., *Science*, 278: 1626-1629 (1997).
Lee et al., *J. Med. Chem.*, 50: 585-589 (2007).
Leung et al., *ChemMedChem*, 4: 329-334 (2009).
Mathew et al., *Chemistry & Biodiversity*, 6: 705-724 (2009).
Morita et al., *J. Med. Chem.*, 38: 2176-2187 (1995).
Natori et al., *Tetrahedron Letters*, 34(35): 5591-5592 (1993).
Schmieg et al., *J. Exp. Med.*, 198:1631-1641 (2003).
Tashiro et al., *Bioorganic & Medicinal Chemistry*, 16: 8896-8906 (2008).
Tashiro et al., *Bioorganic & Medicinal Chemistry*, 17: 6360-6373 (2009).
Tashiro et al., *Tetrahedron Letters*, 49: 6827-6830 (2008).
Watanabe et al., *The Journal of Immunology*, 155: 2972-2983 (1995).
Japanese Patent Office, International Search Report in International Patent Application No. PCT/JP2011/052415 (Apr. 19, 2011).

* cited by examiner

*Primary Examiner* — Traviss C McIntosh, III
(74) *Attorney, Agent, or Firm* — Leydig, Voit & Mayer, Ltd.

(57) ABSTRACT

A compound represented by the following formula (1):

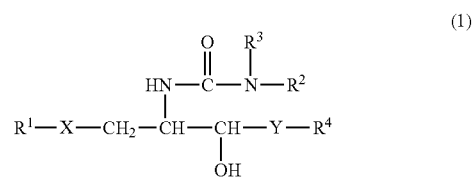

wherein $R^1$ is an aldopyranose residue wherein the 6-hydroxyl group is optionally alkylated, $R^2$ is a $C_{1-26}$ hydrocarbon group optionally having substituent(s), $R^3$ is a hydrogen atom or a $C_{1-26}$ hydrocarbon group optionally having substituent(s), $R^4$ is a $C_{1-21}$ hydrocarbon group optionally having substituent(s), X is an oxygen atom or —$CH_2$—, and Y is —$CH_2$—, —CH(OH)— or —CH=CH—, or a salt thereof is useful for the prophylaxis or treatment of cancer or infection, since it can preferentially induce production of IFN-γ of NKT cells.

13 Claims, 2 Drawing Sheets

SYNTHETIC GLYCOLIPID AND USE THEREOF

CROSS-REFERENCE TO RELATED APPLICATIONS

This patent application is the U.S. national phase of International Patent Application No. PCT/JP2011/052415 filed Feb. 4, 2011, which claims the benefit of Japanese Patent Application No. 2010-024859, filed Feb. 5, 2010, which are incorporated by reference in their entireties herein.

TECHNICAL FIELD

The present invention relates to a novel glycolipid and use thereof, more specifically, a novel glycolipid having a urea bond, a production method thereof and a pharmaceutical use thereof.

BACKGROUND ART

Immune system has a skillful surveillance function to distinguish abnormal cells from autochtonous normal cells in the body and eliminate only the abnormal cells. When the surveillance function collapses, abnormal cells produced by mutation and the like cannot be eliminated, and the presence and growth thereof in the body are allowed. The grown abnormal cell mass is a tumor, or cancer.

The cancer treatment is mainly removal of cancer by surgical operation, or use of anti-cancer agents. However, these treatment methods often place physical burden due to extirpative surgery and side effects of anti-cancer agents, or mental burden due to operative scar on patients.

With such background, treatments by immunotherapy are drawing attention. In the immunotherapy, the number of the patients' own immunocytes is increased, and further activated to attack the cancer cells. As compared to surgical operation, physical burden on the patients due to the treatment is small, and an influence on the patients' social life due to the treatment can be minimized. In addition, a treatment method using immunotherapy and a surgical operation in combination is also employed. Since a tumor minimized by immunotherapy is removed, the physical burden on patients can be reduced. Also, since the operative scar is small, the mental burden can also be drastically reduced.

Natural killer (NK) T cells are immune cells belonging to a new lymphocyte lineage that exhibit characteristics different from those of other lymphocyte lineages (T, B, and NK cells). NKT cells are related to NK cells because cytotoxic perforin granules are present therein (non-patent document 1). However, because NKT cells express not only NK cell markers, but also T cell receptors (TCRs), they have been shown to represent a new class of cells that are distinct from known cells (non-patent document 2). NKT cells can produce both Th1 type cytokine [mainly interferon (IFN)-γ] produced by T helper (Th)1 cell that promotes immunostimulatory action, and Th2 type cytokine [mainly interleukin (IL)-4] produced by Th2 cell that promotes immunosuppressive action (non-patent document 3). In other words, NKT cells can induce both activation and quieting of the immune system, which suggests the possible role of the immune system in the balance adjustment (non-patent document 4). Therefore, it is possible to adjust the collapsed balance of the immune system by controlling the function of NKT cells, which enforces the surveillance function to treat cancer.

The characteristic of NKT cells that is attracting the greatest attention resides in the fact that the α chain of TCR expressed in NKT cells is the same in all the individuals belonging to one certain species. This essentially shows that all NKT cells of the same species of organism are activated by the same substance. As such, the α chain is Vα24 for humans and Vα14 for murine animals, there is a very high homology between the two species. For the β chain, which forms a pair with the α chain, only a very limited number of kinds are known, so this TCR is called "invariant TCR". It is also characteristic that TCR of T cells recognizes a protein fragment, whereas TCR of NKT cells recognizes glycolipid.

A wide variety of sphingoglycolipids are known to exist in living organisms. In general sphingoglycolipids in the living organisms, various sugars or sugar chains are bound to ceramides via β-bonds, and they are present in the cell membranes of various organs (non-patent document 5).

Meanwhile, it is known that sphingoglycolipids comprising sugars bound to ceramides via α-bonds possesses potent immunostimulatory action and antitumor activity (non-patent document 6). α-Galactosylceramides, typified by agelasphins, are glycolipids isolated from extracts from *Agelas mauritianus*, a kind of marine sponge, and have been reported to potently activate NKT cells (non-patent document 7). α-Galactosyl ceramides are taken by antigen presenting cells (APC) represented by dendritic cell (DC) and the like, and presented on a cellular membrane by CD1d protein similar to major histocompatibility complex (MHC) class I molecule. NKT cells are activated by recognizing a complex of the thus-presented CD1d protein and α-galactosylceramide by using TCR, whereby various immune reactions are initiated.

Heretofore, various analogs have been synthesized, and the correlation between the structure and the activity has been researched. It has been clarified that, among the series of synthetized analogs, KRN7000 (compound 1, α-GalCer) developed by Kirin Brewery Co., Ltd. shows the strongest activity, and the corresponding β-form (β-GalCer) does not show an immunostimulatory activity. KRN7000 is sphingoglycolipid comprising a ceramide resulting from the acylation of the sphingosine base by a long-chain fatty acid, and galactose bound thereto in α-configuration (patent document 1, non-patent document 8).

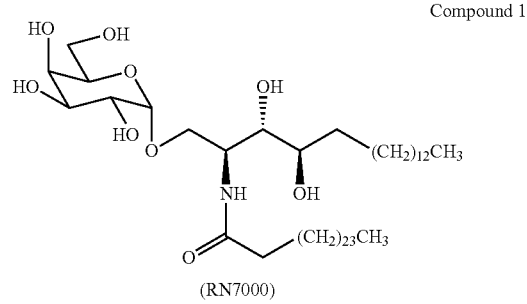

Compound 1 (RN7000)

DOCUMENT LIST

Patent Documents patent document 1: WO98/44928
patent document 2: WO03/105769
patent document 3: WO2007/099999
patent document 4: WO2008/082156

Non-Patent Documents non-patent document 1: Proc. Natl. Acad. Sci., USA, 1998, 95, 5690-5693 non-patent document 2: J. Immunol., 1995, 155, 2972-2983 non-patent document 3: J. Immunol., 1998, 161, 3271-3281 non-patent document 4: Science, 1997, 278, 1623-1626 non-patent document 5: Biochim. Biophys. Acta, 1973, 316, 317-335 non-patent document 6: Tetrahedron Lett., 1993, 34, 5591-5592 non-patent document 7: Science, 1997, 278, 1626-1629 non-patent document 8: J. Med. Chem., 1995, 38, 2176-2187 non-patent document 9: J. Exp. Med., 2003, 198, 1631-1641 non-patent document 10: Bioorg. Med. Chem., 2009, 17, 6360-6373 non-patent document 11: Tetrahedron Lett., 2008, 49, 6827-6830 non-patent document 12: Nature, 2007, 448, 44-49 non-patent document 13: Bioorg. Med. Chem., 2008, 16, 8896-8906 non-patent document 14: ChemMedChem, 2009, 4, 329-334 non-patent document 15: J. Med. Chem., 2007, 50, 585-589 non-patent document 16: Chem. Biodiversity, 2009, 6, 705-724

SUMMARY OF THE INVENTION

Problems to be Solved by the Invention

In recent years, with a focus on the above-described functions of NKT cells, a therapeutic drug of cancer, which contains α-GalCer as an active ingredient, has been developed. However, NKT cells activated by the administration of α-GalCer produce IFN-γ, which is a cytokine useful for the cancer treatment and inducing immunostimulatory activity, as well as simultaneously produce IL-4, which is a cytokine inducing an immunosuppressive action. As a result, the effects of both are cancelled each other, posing the problem of a lack of effect on cancer treatment.

The group of Tsuji et al. has developed a glycolipid, α-C-GalCer, that strongly activates NKT cells of mouse and preferentially produces IFN-γ (compound 2, patent document 2, non-patent document 9). However, since α-C-GalCer hardly shows activity in vitro on human NKT cells, its clinical application is difficult.

On the other hand, we have separately found that novel synthetic glycolipid RCAI-56 (compound 3) having carba-sugar strongly activates NKT cells and induces production of a large amount of IFN-γ (non-patent document 10). We have further found that novel synthetic glycolipid RCAI-61 (compound 4) wherein the 6-hydroxyl group of the sugar moiety of glycolipid is modified is more easily prepared than RCAI-56, and induces production of IFN-γ in large amounts (non-patent document 11). Since RCAI-56 and RCAI-61 show strong activity even in the systems of mouse and human (in vitro), its clinical application is expected.

However, since the synthesis of RCAI-56 requires multiple steps, and the synthesis of RCAI-61 requires complicated modification of sugar, the development of a novel analog permitting more convenient preparation and having an immunostimulatory activity equivalent to or higher than that of RCAI-56 and RCAI-61 has been desired.

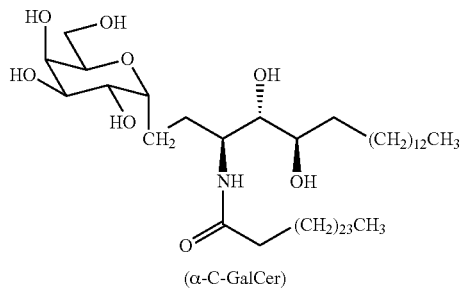

(α-C-GalCer)

Compound 2

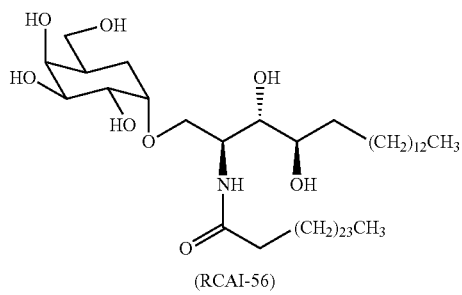

(RCAI-56)

Compound 3

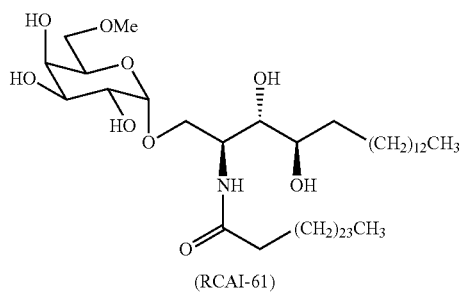

(RCAI-61)

Compound 4

The present invention has been made in view of such actual condition, and its problem to be solved is provision of a novel compound effective for the treatment of cancer and an intermediate useful for the synthesis of the compound and production methods thereof. In addition, it aims to provide a medicament such as a therapeutic drug for cancer and the like, which contains such novel compound.

Means of Solving the Problems

In 2007, the crystal structure analysis of human CD1d-KRN7000-TCR was reported. According to the report, it has been clarified that the sugar moiety of KRN7000 is presented outside the pocket and toward TCR and, on the other hand, the ceramide moiety fits into in the large hydrophobic pocket of CD1d (non-patent document 12). Furthermore, it has been clarified that the amide bond of KRN7000 forms a hydrogen bond with CD1d Thr154 (Thr156 in the case of mouse). Thus, the present inventors have considered that CD1d-glycolipid complex can be stabilized via Thr154 by converting amide bond of glycolipid to other functional group.

Heretofore, analogs wherein the amide bond is converted to a sulfonamide bond: compound 5 (non-patent document 13, patent document 3), analogs with conversion to an α,α-difluoroamide bond: compound 6 (non-patent document 14), analogs with conversion to a 1,2,3-triazole: compound 7 (non-patent document 15, patent document 4) and the like have been reported. However, all of them induce production of mostly Th2 type cytokines such as IL-4 and the like.

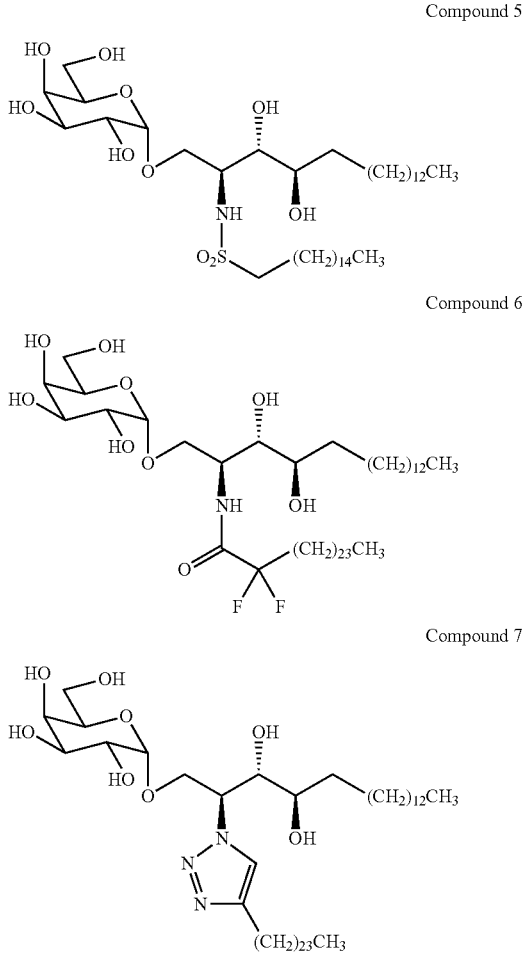

Compound 5

Compound 6

Compound 7

The present inventors considered that the reason therefore may be that these analogs cannot form a strong hydrogen bond with CD1d Thr154 since hydrogen is absent or acidity is high in the amide bond, and therefore, cannot stimulate NKT cells for a long time. That is, the present inventors have considered that the development of an analog having lower acidity of hydrogen than that of amide bond enables more intense stimulation of NKT cells than KRN7000 for a long time.

The inventors have conducted intensive studies based on the above-mentioned hypothesis and developed a production method of a ureide compound wherein an amide bond which is a part of the general skeleton of glycosyl ceramide which is one kind of glycolipid is converted to a urea bond known to have a lower acidity of a hydrogen atom than an amide bond. Further, they have found that ureide compound has a specific immunomodulatory potency, and is extremely effective for the treatment of cancer and infection, which resulted in the completion of the present invention.

Accordingly, the present invention comprises the following.

[1] A compound represented by the following formula (1) or a salt thereof:

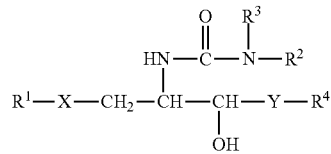

(1)

wherein $R^1$ is an aldopyranose residue wherein the 6-hydroxyl group is optionally alkylated, $R^2$ is a $C_{1-26}$ hydrocarbon group optionally having substituent(s), $R^3$ is a hydrogen atom or a $C_{1-26}$ hydrocarbon group optionally having substituent(s), $R^4$ is a $C_{1-21}$ hydrocarbon group optionally having substituent(s), X is an oxygen atom or —CH$_2$—, and Y is —CH$_2$—, —CH(OH)— or —CH=CH—.

[2] The compound according to the above-mentioned [1], wherein $R^1$ is α-D-galactopyranosyl, or a salt thereof.

[3] The compound according to the above-mentioned [1] or [2], wherein $R^2$ is a $C_{1-26}$ aliphatic hydrocarbon group optionally having substituent(s), and $R^3$ is a hydrogen atom, or a salt thereof.

[4] The compound according to any one of the above-mentioned [1] to [3], wherein $R^4$ is a $C_{1-21}$ alkyl group optionally having substituent(s), or a salt thereof.

[5] The compound according to any one of the above-mentioned [1] to [4], wherein X is an oxygen atom, or a salt thereof.

[6] The compound according to any one of the above-mentioned [1] to [5], wherein Y is —CH(OH)—, or a salt thereof.

[7] A compound represented by the following formula (2) or a salt thereof:

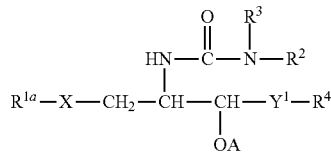

(2)

wherein $R^{1a}$ is an aldopyranose residue wherein the 6-hydroxyl group is optionally alkylated and the hydroxyl groups are protected, $R^2$ is a $C_{1-26}$ hydrocarbon group optionally having substituent(s), $R^3$ is a hydrogen atom or a $C_{1-26}$ hydrocarbon group optionally having substituent(s), $R^4$ is a $C_{1-21}$ hydrocarbon group optionally having substituent(s), X is an oxygen atom or —CH$_2$—, $Y^1$ is —CH$_2$—, —CH(OA)- or —CH=CH—, and A is a hydrogen atom or a hydroxyl-protecting group.

[8] A pharmaceutical composition comprising a compound represented by the above-mentioned formula (1) or a salt thereof, and a pharmacologically acceptable carrier.

[9] An agent for the prophylaxis or treatment of cancer, comprising a compound represented by the above-mentioned formula (1), or a salt thereof.

[10] An NKT cell activator comprising a compound represented by the above-mentioned formula (1), or a salt thereof.

[11] A selective IFN-γ production inducer comprising a compound represented by the above-mentioned formula (1), or a salt thereof.

[12] An agent for the prophylaxis or treatment of infection comprising a compound represented by the above-mentioned formula (1), or a salt thereof.

[13] A compound represented by the above-mentioned formula (1) or a salt thereof, for use in the prophylaxis or treatment of cancer.

[14] A compound represented by the above-mentioned formula (1) or a salt thereof, for use in the activation of NKT cell.

[15] A compound represented by the above-mentioned formula (1) or a salt thereof, for use in the induction of selective IFN-γ production.

[16] A compound represented by the above-mentioned formula (1) or a salt thereof, for use in the prophylaxis or treatment of infection.

[17] A method for the prophylaxis or treatment of cancer, comprising administering an effective amount of a compound represented by the above-mentioned formula (1) or a salt thereof to a mammal.

[18] A method of activating NKT cell, comprising administering an effective amount of a compound represented by the above-mentioned formula (1) or a salt thereof to a mammal.

[19] A method of inducing selective IFN-γ production, comprising administering an effective amount of a compound represented by the above-mentioned formula (1) or a salt thereof to a mammal.

[20] A method for the prophylaxis or treatment of infection, comprising administering an effective amount of a compound represented by the above-mentioned formula (1) or a salt thereof to a mammal.

[21] Use of a compound represented by the above-mentioned formula (1) or a salt thereof for the production of an agent for the prophylaxis or treatment of cancer.

[22] Use of a compound represented by the above-mentioned formula (1) or a salt thereof for the production of an NKT cell activator.

[23] Use of a compound represented by the above-mentioned formula (1) or a salt thereof for the production of a selective IFN-γ production inducer.

[24] Use of a compound represented by the above-mentioned formula (1) or a salt thereof for the production of an agent for the prophylaxis or treatment of infection.

[25] A method of producing a compound represented by the following formula (1) or a salt thereof, comprising the following steps (a) to (c):

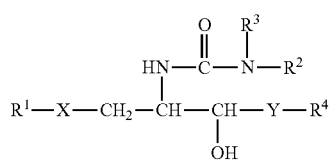

(1)

wherein $R^1$ is an aldopyranose residue wherein the 6-hydroxyl group is optionally alkylated, $R^2$ is a $C_{1-26}$ hydrocarbon group optionally having substituent(s), $R^3$ is a hydrogen atom or a $C_{1-26}$ hydrocarbon group optionally having substituent(s), $R^4$ is a $C_{1-21}$ hydrocarbon group optionally having substituent(s), X is an oxygen atom or —$CH_2$—, and Y is —$CH_2$—, —$CH(OH)$— or —$CH=CH$—, (a) reacting a compound represented by the following formula (3)

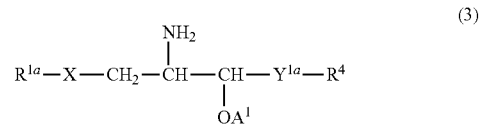

(3)

wherein $R^{1a}$ is an aldopyranose residue wherein the 6-hydroxyl group is optionally alkylated and the hydroxyl groups are protected, $R^4$ is a $C_{1-21}$ hydrocarbon group optionally having substituent(s), X is an oxygen atom or —$CH_2$—, and $Y^{1a}$ is —$CH_2$—, —$CH(OA^1)$- or —$CH=CH$—, and $A^1$ is a hydroxyl-protecting group, or a salt thereof, with a compound represented by the following formula (4) or (5):

(4)

(5)

wherein $R^2$ is a $C_{1-26}$ hydrocarbon group optionally having substituent(s), $R^3$ is a hydrogen atom or a $C_{1-26}$ hydrocarbon group optionally having substituent(s), and L is a leaving group to give a compound represented by the following formula (2'):

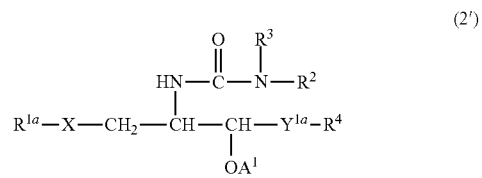

(2')

wherein each symbol is as defined above, or a salt thereof;
(b) deprotecting $A^1$ in a compound represented by the formula (2') or a salt thereof to give a compound represented by the following formula (2"):

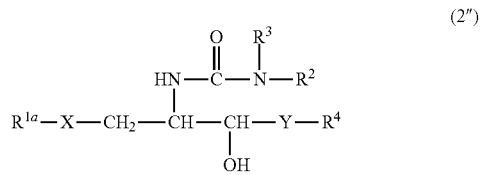

(2")

wherein each symbol is as defined above, or a salt thereof; and
(c) removing the hydroxyl-protecting group at $R^{1a}$ of the compound represented by the formula (2") or a salt thereof to give a compound represented by the formula (1) or a salt thereof.

Effect of the Invention

A ureidoglycolipid having a urea bond, which was developed by the inventors, can form a complex with a CD1d protein of an antigen presenting cell (APC), which complex being stronger than KRN7000.

A ureidoglycolipid having a urea bond, which was developed by the inventors can be synthesized very easily, and can intensely activate NKT cells even with a trace amount. Therefore, since it can produce IFN-γ in a larger amount than the existing compounds having an amide bond, a small amount of administration can provide sufficient efficacy.

DESCRIPTION OF EMBODIMENTS

Figure 1:
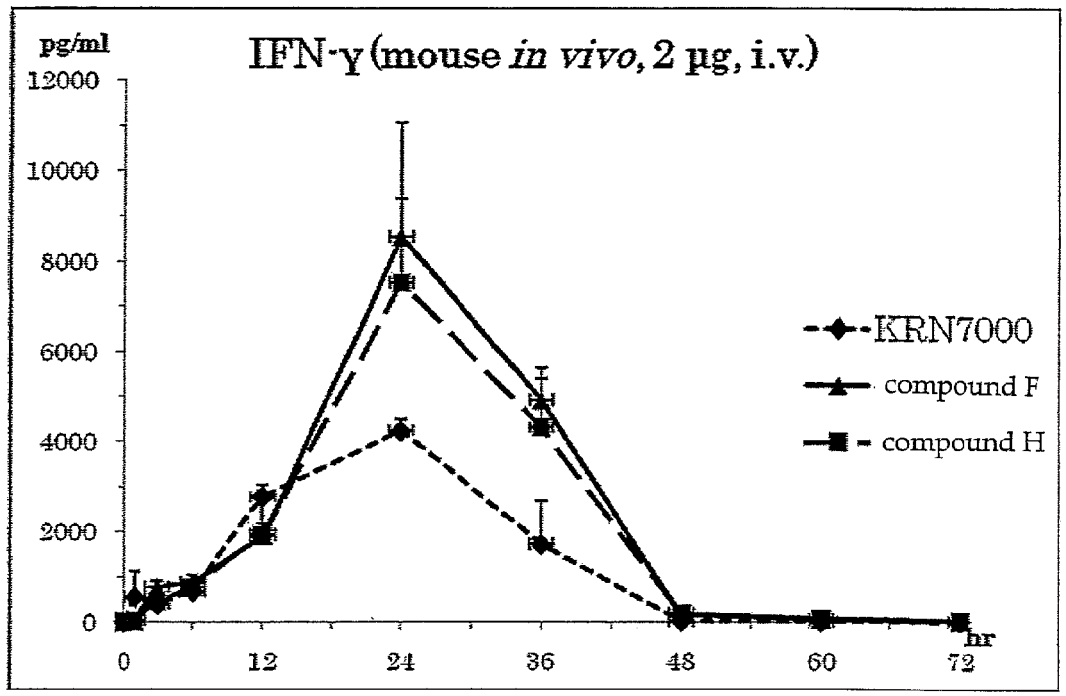
FIG. 1 shows IFN-γ concentration in mouse plasma after lapse of indicated time after administration of a synthetic glycolipid to mice in vivo (Experimental Example 1).

The present invention is explained in detail in the following by referring to preferable embodiments.

First, the definitions of the symbols to be used in each formula of the present invention are explained.

$R^1$ is an aldopyranose residue wherein 6-hydroxyl group is optionally alkylated, and $R^{1a}$ is an aldopyranose residue wherein the 6-hydroxyl group is optionally alkylated and the hydroxyl groups are protected, wherein the aldopyranose residue means a residue excluding the reduced terminal hydroxyl group of aldopyranose. Examples of the aldopyranose residue include α-D-galactopyranosyl, α-D-glucopyranosyl, β-D-galactopyranosyl, β-D-glucopyranosyl and the like. Particularly, α-D-galactopyranosyl is preferable from the aspect of pharmacological effect.

The "aldopyranose residue wherein the 6-hydroxyl group is optionally alkylated and the hydroxyl groups are protected" means that when the 6-hydroxyl group of the aldopyranose residue is alkylated, all other remaining hydroxyl groups are protected, and when the 6-hydroxyl group is not alkylated, all hydroxyl groups are protected.

Examples of the alkyl group when the 6-hydroxyl group of the aldopyranose residue is alkylated include chain, branched chain, or cyclic alkyl group (preferably carbon number 1 to 24, more preferably carbon number 1 to 16, still more preferably carbon number 1 to 10, particularly preferably carbon number 1 to 6) such as methyl group, ethyl group, n-propyl group, isopropyl group, n-butyl group, isobutyl group, sec-butyl group, tert-butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, cyclopentyl group, cyclohexyl group and the like, with preference given to methyl group.

Examples of the hydroxyl-protecting group of sugar of the aldopyranose residue include acyl group, tert-butyldimethylsilyl (TBS) group, trimethylsilyl (TMS) group, benzyl (Bn) group, p-methoxybenzyl (PMB) group and the like.

In the present specification, the acyl group means a formyl group; a $C_{1-12}$ linear or branched, or a $C_{3-10}$ cyclic, alkyl-carbonyl group (e.g., acetyl group, propionyl group, butyryl group, isobutyryl group, valeryl group, pivaloyl group, hexanoyl group); $C_{2-12}$ straight chain or branched, or a $C_{3-10}$ cyclic alkenyl-carbonyl group (e.g., acryloyl group, methacryloyl group); or a $C_{6-14}$ aryl-carbonyl group (e.g., benzoyl group, naphthoyl group). The aryl group of the aryl-carbonyl group is a monocyclic-tricyclic aromatic hydrocarbon group, such as a phenyl group, a naphthyl group, an anthryl group and a phenanthryl group. Of these, as the acyl group, a formyl group, an acetyl group, a propionyl group, a butyryl group, an isobutyryl group, a benzoyl group, a naphthoyl group and the like are preferable, and an acetyl group and a benzoyl group are more preferable.

As the hydroxyl-protecting group of the sugar of the aldopyranose residue, a benzyl (Bn) group and a p-methoxybenzyl (PMB) group are preferable.

$R^2$ is a $C_{1-26}$ hydrocarbon group optionally having substituent(s). The hydrocarbon group is a concept encompassing substituted or unsubstituted aliphatic hydrocarbons such as $C_{1-26}$ alkyl group, $C_{2-26}$ alkenyl group, $C_{2-26}$ alkynyl group, $C_{3-26}$ cycloalkyl group, $C_{3-26}$ cycloalkenyl group and the like, aromatic hydrocarbons such as $C_{6-14}$ aryl group and the like, which may be any of linear, branched chain and cyclic forms, a saturated hydrocarbon group or an unsaturated hydrocarbon group, and optionally has an unsaturated bond in a molecule or on a terminal. Of these, substituted or unsubstituted $C_{1-26}$ aliphatic hydrocarbon group is preferable, and substituted or unsubstituted $C_{1-26}$ alkyl group is more preferable. While the carbon number of $R^2$ is 1 to 26, it is preferably 16 to 26, more preferably 20 to 24. When the carbon number exceeds 26, the selectivity of the activity decreases.

Examples of the substituent of the hydrocarbon group include halogen (preferably chlorine atom, fluorine atom); chain, branched chain, or cyclic alkyl group (preferably carbon number 1 to 24, more preferably carbon number 1 to 16, more preferably carbon number 1 to 10, particularly preferably carbon number 1 to 4) such as methyl group, ethyl group, n-propyl group, isopropyl group, n-butyl group, isobutyl group, sec-butyl group, tert-butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, cyclopentyl group, cyclohexyl group and the like; a chain, branched chain, or cyclic alkenyl group (preferably carbon number 2 to 24, more preferably carbon number 2 to 16, still more preferably carbon number 2 to 10, particularly preferably carbon number 2 to 4) such as vinyl group, propenyl group, butenyl group and the like; chain, branched chain, or cyclic alkynyl group (preferably carbon number 2 to 24, more preferably carbon number 2 to 16, still more preferably carbon number 2 to 10, particularly preferably carbon number 2 to 4) such as ethynyl group, propargyl group, butynyl group, pentynyl group and the like; aryl group (preferably carbon number 6 to 14) such as phenyl group and the like; chain, branched chain, or cyclic alkoxy group (preferably carbon number 1 to 24, more preferably carbon number 1 to 16, more preferably carbon number 1 to 10, particularly preferably carbon number 1 to 4) such as methoxy group, ethoxy group, propoxy group, isopropoxy group, butoxy group, tert-butoxy group and the like; aryloxy group (preferably carbon number 6 to 14) such as phenoxy group and the like; electron-donating group such as hydroxyl group; amino group; mono- or di-alkyl (as defined for alkyl group) amino group such as methylamino group, dimethylamino group, ethylamino group, diethylamino group and the like, and the like; and electron-withdrawing group such as carboxyl group; alkoxy (as defined for alkoxy group) carbonyl group; acyl group (preferably straight chain, branched chain or cyclic alkyl-carbonyl group having a carbon number of 1 to 24); carbamoyl group; straight chain, branched chain or cyclic haloalkyl group (preferably carbon number 1 to 24, more preferably carbon number 1 to 16, more preferably carbon number 1 to 10, particularly preferably carbon number 1 to 4) such as trifluoromethyl group and the like; alkyl (as defined for alkyl group) carbonylamino group such as acetamide group and the like, aryl (preferably carbon number 6 to 14) carbonylamino group such as benzoylamino group and the like, and the like. The above-mentioned alkyl group, alkyl moiety of the alkoxy group, aryl group and the like may be substituted by at least one kind from the aforementioned halogen, alkyl group, alkenyl group, alkynyl group, aryl group, alkoxy group, hydroxyl group, amino group and alkylamino group, or these substituents may be bonded to form a ring.

The number of the substituent is not particularly limited and, for example, it is appropriately selected from 1 to 4. When the number of the substituent is two or more, they may be the same or different.

$R^3$ is a hydrogen atom or a $C_{1-26}$ hydrocarbon group optionally having substituent(s). As the "$C_{1-26}$ hydrocarbon group optionally having substituent(s)", a group similar to "$C_{1-26}$ hydrocarbon group optionally having substituent(s)" for $R^2$ can be mentioned. $R^3$ is preferably a hydrogen atom.

$R^4$ is a $C_{1-21}$ hydrocarbon group optionally having substituent(s). Examples of the hydrocarbon group include substituted or unsubstituted aliphatic hydrocarbon group such as alkyl group having a carbon number of 1 to 21, alkenyl group having a carbon number of 2 to 21, alkynyl group having a carbon number of 2 to 21, cycloalkyl group having a carbon number of 3 to 14, cycloalkenyl group having a carbon number of 3 to 14 and the like, aromatic hydrocarbon group such as aryl group having a carbon number of 6 to 14 and the like, which may be linear, branched or cyclic, or may be a saturated hydrocarbon group or an unsaturated hydrocarbon group, and optionally having an unsaturated bond in a molecule or at the terminal. As such hydrocarbon group, a substituted or unsubstituted $C_{1-21}$ alkyl group is preferable. As the substituent of such hydrocarbon group, those similar to the aforementioned substituent of the hydrocarbon group for $R^2$ can be mentioned. The number of the substituent is not particularly limited and can be appropriately selected from, for example, 1 to 4. When the number of the substituent is two or more, they may be the same or different.

Preferred as $R^4$ is a linear alkyl group. While the carbon number of $R^4$ is 1 to 21, it is preferably 1 to 15, more preferably 10 to 15. When the carbon number exceeds 21, the effect of the invention is difficult to obtain.

X is an oxygen atom or —$CH_2$—, with preference given to an oxygen atom.

Y is —$CH_2$—, —CH(OH)— or —CH=CH—, with preference given to —CH(OH)—.

$Y^1$ is —$CH_2$—, —CH(OA)- or —CH=CH—, with preference given to —CH(OA)-.

$Y^{1a}$ is —$CH_2$—, —CH(OA$^1$)- or CH=CH—, with preference given to —CH(OA$^1$)-.

A is a hydrogen atom or a hydroxyl-protecting group, and as the hydroxyl-protecting group, an acyl group (as defined above), a tert-butyldimethylsilyl (TBS) group, a benzyl (Bn) group, a p-methoxybenzyl (PMB) group, an acetonide group and the like can be mentioned. Of these, when X is an oxygen atom, a TBS group is preferable, and when X is —$CH_2$—, an acetonide group is preferable.

$A^1$ is a hydroxyl-protecting group, and as the hydroxyl-protecting group, a group similar to the hydroxyl-protecting group for A can be mentioned.

L is a leaving group, and as the leaving group, a halogen atom (e.g., chlorine atom, bromine atom), an imidazolyl group and the like can be mentioned.

A compound represented by the general formula (1) above (hereinafter referred to as "compound (1)"; the same applies to the designation of compounds represented by respective formulas) involves α-form and β-form structural isomers resulting from the aldopyranose residue, and may be in the α-form, β-form or a mixture thereof, with preference given to the α-form from the viewpoint of pharmacological effect.

Compound (1) has at least four kinds of optical isomers resulting from the asymmetric carbon in the lipid moiety thereof; in the present invention, compound (1) may be a single optically active substance, or a mixture of two or more kinds of optically active substances in an optionally chosen ratio (including racemates). The asymmetric carbon to which —NHC(=O)NR$^2$(R$^3$) is bonded is preferably in an S configuration, and the asymmetric carbon to which OH is bonded is preferably in a configuration of the relationship of anti with the asymmetric carbon to which —NHC(=O)NR$^2$(R$^3$) is bonded. When Y is —CH(OH)—, the asymmetric carbon in —CH(OH)— is preferably in the R-configuration; this also applies to $Y^1$ and $Y^{1a}$.

For compounds (2), (2'), (2") and (3), those shown above can be mentioned as suitable.

Salts of compound (1) are preferably pharmacologically acceptable salts; examples include inorganic acid salts such as hydrochlorides, hydrobromides, hydroiodides, sulfates, nitrates, and phosphates; organic acid salts such as succinates, fumarates, acetates, methanesulfonates, and toluenesulfonates; alkali metal salts such as sodium salts and potassium salts; alkaline earth metal salts such as magnesium salts and calcium salts; ammonium salts such as ammonium salts and alkylammonium salts; and the like. The same applies to compounds (2), (2'), (2") and (3).

Specific examples of preferable compound (1) of the present invention are shown in Table 1, which is not to be construed as limitative.

TABLE 1

| compound | $R^1$ | $R^2$ | $R^3$ | $R^4$ | X | Y |
|---|---|---|---|---|---|---|
| F | (sugar with OH, OH, HO, OH, O) | —(CH$_2$)$_{23}$CH$_3$ | H | —(CH$_2$)$_{13}$CH$_3$ | O | —CH(OH)— |

TABLE 1-continued

![structure]

| compound | R¹ | R² | R³ | R⁴ | X | Y |
|---|---|---|---|---|---|---|
| G | galactopyranosyl (OH, OH, OH, HO-, OH) | —(CH₂)₁₅CH₃ | H | —(CH₂)₁₃CH₃ | O | —CH(OH)— |
| H | 6-O-methyl-galactopyranosyl (OMe, OH, HO-, OH) | —(CH₂)₂₃CH₃ | H | —(CH₂)₁₃CH₃ | O | —CH(OH)— |
| I | galactopyranosyl (OH, OH, HO-, OH) | —(CH₂)₇CH₃ | H | —(CH₂)₁₃CH₃ | O | —CH(OH)— |
| J | galactopyranosyl (OH, OH, HO-, OH) | —(CH₂)₅—C₆H₅ | H | —(CH₂)₁₃CH₃ | O | —CH(OH)— |

Among those, particularly preferable compounds are the following compounds.

[1] (2S,3S,4R)-1-(α-D-galactopyranosyloxy)-2-(tetracosylureido)-3,4-octadecanediol (compound F)
[2] (2S,3S,4R)-1-(α-D-galactopyranosyloxy)-2-(hexadecylureido)-3,4-octadecanediol (compound G)
[3] (2S,3S,4R)-1-(6-O-methyl-α-D-galactopyranosyloxy)-2-(tetracosylureido)-3,4-octadecanediol (compound H)

Preferable embodiment of the production method of the compound of the present invention is now explained. The compound of the present invention can be produced by various methods. Compound (1) wherein X is an oxygen atom can be produced, for example, according to the method described in the following Scheme 1.

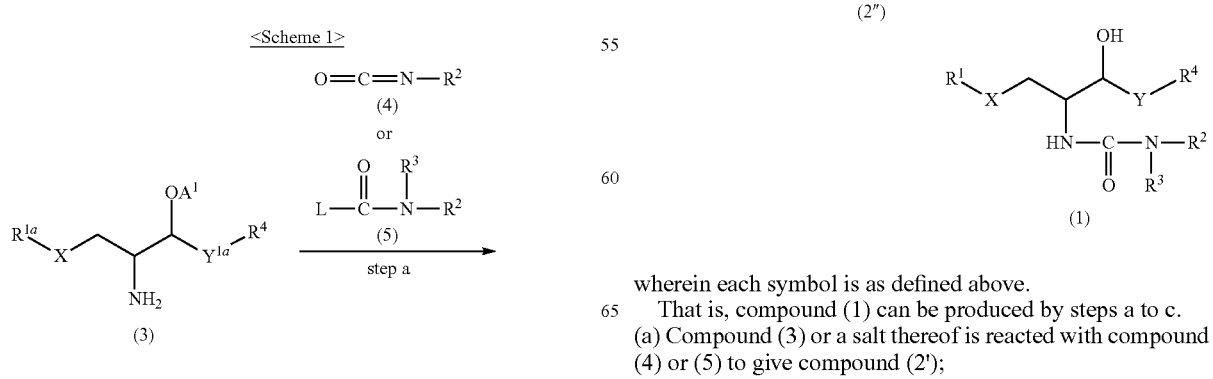

wherein each symbol is as defined above.

That is, compound (1) can be produced by steps a to c.

(a) Compound (3) or a salt thereof is reacted with compound (4) or (5) to give compound (2');

(b) $A^1$ in compound (2') or a salt thereof is deprotected to give compound (2") or a salt thereof; and (c) the hydroxyl-protecting group for $R^{1a}$ in compound (2") or a salt thereof is deprotected to give compound (1) or a salt thereof.

(Step a)

In step a, compound (3) is subjected to urea synthesis to give compound (2'). Specifically, compound (3) is reacted with compound (4) or (5) in a solvent, in the presence of a base where necessary.

While the solvent is not particularly limited as long as the reaction is not inhibited, for example, halogen solvents (e.g., dichloromethane, chloroform) are preferably used.

Where necessary, a base may be added. When compound (5) is used, a base is preferably used. As such base, pyridine, triethylamine and the like can be mentioned, with preference given to pyridine.

The amount of the solvent to be used is generally 5- to 100-fold amount, preferably 20- to 50-fold amount, relative to compound (3).

The amount of the base to be used is generally 10 to 50 equivalents, preferably 10 to 20 equivalents, relative to compound (3).

The amount of compound (4) or (5) to be used is generally 1 to 20 equivalents, preferably 1 to 10 equivalents, relative to compound (3).

The reaction temperature is generally −20° C. to room temperature, preferably 0 to 4° C., and the reaction time is generally 1 to 24 hr, preferably 6 to 12 hr.

After completion of the reaction, compound (2') can be isolated and purified by a conventional method. For example, the reaction mixture is diluted with water, and extracted with an ether solvent such as diethyl ether and the like, an ester solvent such as ethyl acetate and the like. When pyridine is used as a base, the obtained organic layer is washed with saturated aqueous copper sulfate solution, washed with water, saturated brine etc., and dried over anhydrous magnesium sulfate etc. After filtration, the filtrate is concentrated under reduced pressure, and the residue is purified by column chromatography and the like to give compound (2').

(Step b)

In step b, the hydroxyl-protecting group for $A^1$ in the lipid moiety of compound (2') is deprotected to give compound (2"). The deprotection method is selected from known methods according to the kind of the protecting group. When, for example, $A^1$ is a tert-butyldimethylsilyl (TBS) group, compound (2') is reacted with tetrabutylammonium fluoride or an acid in a solvent.

As the acid, a strong acid such as trifluoroacetic acid, p-toluenesulfonic acid, hydrochloric acid and the like is preferably used. The amount of the acid to be used is generally catalytic amount to 10 equivalents, preferably 1 to 2 equivalents, relative to compound (2').

The amount of tetrabutylammonium fluoride to be used is generally 2 equivalents to 20 equivalents, preferably 4 to 10 equivalents, relative to compound (2').

The reaction temperature is generally −20° C. to room temperature, preferably −10 to 0° C., and the reaction time is generally 1 to 24 hr, preferably 2 to 12 hr.

As the solvent, a water-soluble solvent is preferable, and tetrahydrofuran is particularly preferable. The amount of the solvent to be used is generally 5- to 100-fold amount, preferably 10- to 50-fold amount, relative to compound (2').

After completion of the reaction, compound (2") can be isolated and purified by a conventional method. For example, the reaction mixture is diluted with water, and extracted with an ether solvent such as diethyl ether and the like, an ester solvent such as ethyl acetate and the like. The obtained organic layer is washed with water, saturated brine etc., and dried over anhydrous magnesium sulfate etc. After filtration, the filtrate is concentrated under reduced pressure, and the residue is purified by column chromatography and the like to give compound (2").

(Step c)

In step (c), the hydroxyl-protecting groups of aldopyranose in compound (2") are deprotected to give compound (1). The deprotection method is selected from known methods according to the kind of the protecting group. For example, in the case of a benzyl group, compound (2") is reacted in the presence of hydrogen and a catalyst in a solvent.

As the solvent, a mixed solvent of an alcohol solvent and a halogen solvent is preferable, and a mixed solvent of ethanol and chloroform is more preferable. The amount of the solvent to be used is generally 10- to 100-fold amount, preferably 10- to 50-fold amount, relative to compound (2").

As the reduction catalyst, palladium hydroxide, platinum oxide, Raney-nickel and the like can be mentioned. The amount of the reduction catalyst to be used is sufficiently a catalytic amount relative to compound (2").

The reaction time is generally 1 to 24 hr, preferably 12 to 24 hr. The reaction temperature is 0° C. to room temperature, preferably room temperature.

After completion of the reaction, the reaction mixture is filtered, the filtrate is concentrated under reduced pressure, and the residue is purified by column chromatography to give the object compound (1) in a high yield.

When the obtained compound (1) contains an isomer, the isomers (α-form and β-form) may be separated and purified by column chromatography using solvents with different polarity. In addition, the isomers may be separated and purified in each step of steps (a) and (b) and, for example, the isolated α-form may be used as the starting compound of the next step to give α-form of compound (1).

Compounds (2') and (2"), which are intermediates for the above-mentioned production methods, can be collectively represented by the formula (2):

$$R^{1a}-X-CH_2-\underset{OA}{\underset{|}{CH}}-\underset{}{\underset{}{CH}}-Y^1-R^4 \quad \text{with} \quad HN-\overset{O}{\overset{\|}{C}}-\underset{R^2}{\underset{|}{N}}-R^2, \quad R^3 \text{ on N} \tag{2}$$

wherein each symbol is as defined above. Compound (2) is a useful, novel compound for the production of compound (1).

Compound (3), which is a starting material of the above-mentioned Scheme 1, can be produced according to the method described in Bioorganic & Medicinal Chemistry, 2008, 16, 8896-8906, specifically, the method described in the following Scheme 2.

<Scheme 2>

HX—CH$_2$—CH(NH$_2$)—CH(OH)—Y—R$^4$  $\xrightarrow{\text{step 1}}$ (a)

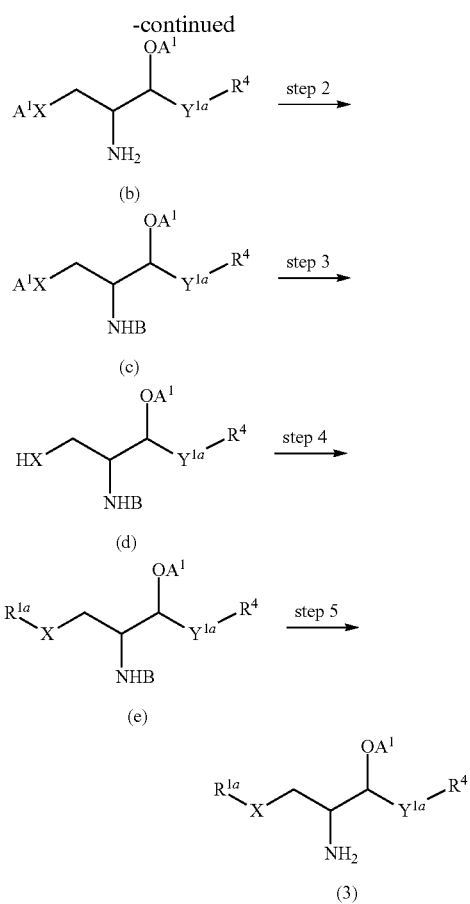

(Step 1)

Step 1 is a step for protecting the —XH and hydroxyl group of amino alcohol (a) to give compound (b). Specifically, amino alcohol (a) is reacted with a protecting reagent in the presence of a base in an organic solvent. Bases include amino compounds such as pyridine, 2,6-lutidine, and triethylamine. An organic silylating reagent is suitably used as the protecting reagent; for example, tert-butyldimethylsilyl trifluoromethanesulfonate, tert-butyldimethylsilyl chloride and the like can be used. Any solvent that does not interfere with this reaction can be used; for example, halogen solvents (e.g., dichloromethane, chloroform) are suitable. The amount of base used is normally 10 to 50 fold by volume, preferably 10 to 20 fold by volume, relative to amino alcohol (a). The amount of protecting reagent used is normally 1 to 5 equivalents, preferably 1 to 2 equivalents, per hydroxyl group of amino alcohol (a). Reaction temperature is normally −20° C. to room temperature, preferably 0 to 4° C.; reaction time is normally 1 to 48 hours, preferably 12 to 24 hours. After completion of the reaction, the reaction mixture is concentrated under reduced pressure, and the residue is purified by column chromatography, whereby compound (b) can be obtained at high percent yields.

(Step 2)

Step 2 is a step for protecting the amino group of compound (b) to give compound (c). In the formula (c), B is an amino-protecting group. Specifically, compound (b) is reacted with an amino group protecting reagent in an organic solvent. Examples of protecting reagents include 9-fluorenylmethyl succinimidyl carbonate, di-tert-butyl dicarbonate, and benzyl chloroformate. The amount of protecting reagent used is normally 1 to 5 equivalents, preferably 1 to 2 equivalents, relative to compound (b). As the solvent, for example, aprotic solvents are suitable, which may be used in a mixture of two or more kinds. The amount of solvent used is normally 10 to 50 fold by volume, preferably 20 to 30 fold by volume, relative to compound (b). Reaction temperature is normally 0° C. to room temperature, preferably room temperature; reaction time is normally 1 to 50 hours, preferably 12 to 24 hours. After completion of the reaction, the reaction mixture is diluted with water, and extracted with a solvent such as ether. The organic layer obtained is washed with water, saturated sodium hydrogen carbonate and the like, and dried with anhydrous magnesium sulfate and the like, after which it is filtered. The filtrate is concentrated under reduced pressure, and the residue is purified by column chromatography, whereby compound (c) can be obtained at high percent yields.

(Step 3)

Step 3 is a step for removing the protecting group $A^1$ in —$XA^1$ in compound (c) to give compound (d). A method of removal is chosen according to the protecting group; for example, compound (c) and an acid are reacted in a solvent. As the acid, strong acids such as trifluoroacetic acid, p-toluenesulfonic acid, and hydrochloric acid are suitably used. The amount of acid used is normally a catalytic amount to 10 fold by volume, preferably 1 to 2 fold by volume, relative to compound (c). Reaction temperature is normally −20° C. to room temperature, preferably −10 to 0° C.; reaction time is normally 2 to 12 hours, preferably 2 to 4 hours. The solvent is preferably a water-soluble solvent, and tetrahydrofuran is particularly preferable. The amount of solvent used is normally 5 to 100 fold by volume, preferably 10 to 50 fold by volume, relative to compound (c). After completion of the reaction, compound (d) can be isolated and purified by a conventional method. For example, the reaction mixture is neutralized with a basic aqueous solution such as an aqueous solution of sodium hydroxide, and extracted with an ether solvent such as diethyl ether. The organic layer obtained is washed with a saturated aqueous solution of sodium hydrogen carbonate, saturated brine and the like, and dried with anhydrous potassium carbonate and the like. After the solution is filtered, the filtrate is concentrated under reduced pressure, and the residue may be purified by column chromatography.

(Step 4)

Step 4 is a step for aldopyranosylating compound (d) to give compound (e). The aldopyranosylation is achieved by, for example, reacting compound (d) with an aldopyranosyl halide whose hydroxyl groups are protected ($R^{1a}$—$X^1$, $X^1$ is a halogen) in a solvent in the presence of an activator. Examples of the activator include a combination of tin chloride and silver perchlorate, silver trifluoromethanesulfonate and the like. Furthermore, this reaction is desirably carried out in the presence of a dehydrant such as molecular sieves. The amount of activator used is normally 2 to 4 equivalents, preferably 2 to 3 equivalents, relative to compound (d). The amount of dehydrant used is normally 2 to 10 fold by weight, preferably 3 to 5 fold by weight, relative to compound (d). The aldopyranosyl halide whose hydroxyl groups are protected is preferably one wherein the hydroxyl groups at the 2,3,4,6-positions are protected by a benzyl (Bn) group; the halogen is preferably a fluorine atom. The amount used of aldopyranosyl halide whose hydroxyl groups are protected is normally 2 to 4 equivalents, preferably 2 to 3 equivalents, relative to compound (d). Reaction temperature is normally −20° C. to room temperature; reaction time is normally 2 to 12 hours, preferably 2 to 4 hours. The solvent is preferably an aprotic solvent, and tetrahydrofuran is particularly preferable. The amount of solvent used is normally 10 to 100 fold by volume, preferably 20 to 50 fold by volume, relative to compound (d). After completion of the reaction, the reaction mixture is filtered, and the filtrate is washed with saturated brine and the like and dried with anhydrous magnesium sulfate and the like. After the solution is filtered, the filtrate is concentrated under reduced pressure, and the residue is purified by column chromatography, whereby compound (e) can be obtained.

(Step 5)

Step 5 is a step for removing the protecting group B for the amino group of compound (e) to give compound (3). A method of removal is chosen according to the protecting group; for example, compound (e) is reacted in a solvent in the presence of a base. Examples of the solvent include aprotic solvents, with preference given to DMF. As the base, morpholine, piperidine and the like are suitably used. The amount of solvent used is normally 10 to 200 fold by volume, preferably 20 to 50 fold by volume, relative to compound (e). The amount of base used is normally 10 to 200 equivalents, preferably 100 to 200 equivalents, relative to compound (e). Reaction temperature is normally −20° C. to room temperature, preferably room temperature. Reaction time is normally 0.5 to 12 hours, preferably 5 to 10 hours. After completion of the reaction, the solvent of the reaction mixture is replaced as required, and the reaction mixture is washed with water, saturated brine and the like, and dried with anhydrous potassium carbonate and the like. After the solution is filtered, the filtrate is concentrated under reduced pressure, and the residue is purified by column chromatography, whereby compound (3) can be obtained at high percent yields.

In addition, compounds (4) and (5), which are starting materials of the above-mentioned Scheme 1, can be produced by a method known per se.

For example, carboxylic acid represented by $R^2CO_2H$ is subjected to Curtius rearrangement reaction to give compound (4). Specifically, (1) carboxylic acid represented by $R^2CO_2H$ is reacted with a halogenating agent such as thionyl chloride, oxalyl chloride and the like to give an acid halide, which is then reacted with an azide salt such as sodium azide and the like, or (2) carboxylic acid represented by $R^2CO_2H$ is reacted with diphenylphosphoryl azide in the presence of a base such as triethylamine and the like to give acyl azide, which is then heated etc. to allow progress of the rearrangement reaction, whereby compound (4) can be produced.

In addition, amine represented by $R^2NH_2$ or $R^2(R^3)NH$ is reacted with triphosgene or carbonyldiimidazole by a method known per se to give compound (4) and (5), respectively.

Compound (1) wherein X is —$CH_2$— can be obtained by, for example, obtaining compound (3) wherein X is —$CH_2$— according to the method described in Tetrahedron Lett., 2005, 46, 5043-5047, obtaining compound (2') in the same manner as in the above-mentioned step a, then removing the hydroxyl-protecting group $A^1$ in the lipid moiety of compound (2') in the same manner as in step b to give compound (2"), followed by the same manner as in the above-mentioned step c to give compound (1) wherein X is —$CH_2$—.

Compound (1) wherein the 6-hydroxyl group of the aldopyranose residue is alkylated can be obtained by obtaining compound (3) wherein the 6-hydroxyl group of aldopyranose residue is alkylated according to the method described in, for example, Tetrahedron Lett., 2008, 49, 6827, obtaining compound (2') in the same manner as in the above-mentioned step a, then removing the hydroxyl-protecting group $A^1$ in the lipid moiety of compound (2') in the same manner as in step b to give compound (2"), followed by the same manner as in the above-mentioned step c to give compound (1) wherein the 6-hydroxyl group of the aldopyranose residue is alkylated.

Now, the agent for the prophylaxis or treatment of cancer or infections and the like, NKT cell activator, and selective IFN-γ production inducer of the present invention are explained.

By the administration of compound (1) or a salt thereof of the present invention (hereinafter to be referred to as "compound (1) and the like"), NKT cell can be activated, IFN-γ production can be selectively and preferentially induced, and production of IL-4 can be suppressed unlike α-galactosylceramide. Therefore, the prophylaxis or treatment of cancer or infection and the like is possible without aggravating the disease state. Since compound (1) and the like have a urea bond, they have lower acidity than with the hydrogen atom of the amide bond, as a result of which they form a strong hydrogen bond with Thr154 of CD1d protein in APC, thereby forming a strong complex. Consequently, NKT cells can be intensely activated for a long time. Furthermore, even with a smaller dose of administration than that of α-galactosylceramide, NKT cells can be potently activated to increase the amount of IFN-γ produced.

For compound (1) and the like, the α-form and the β-form can be used alone or in combination; however, from the viewpoint of pharmacological effect, the α-form is preferred.

The diseases that can be prevented or treated by compound (1) and the like of the present invention are not particularly limited as long as increase of IFN-γ production is expected to show a direct or indirect prophylactic or therapeutic effect thereon. Examples thereof include various carcinomas (e.g., breast cancer, colorectal cancer, lung cancer, prostate cancer, esophagus cancer, gastric cancer, liver cancer, biliary cancer, spleen cancer, kidney cancer, urinary bladder cancer, uterine cancer, testis cancer, thyroid cancer, pancreatic cancer, brain tumor, ovarian cancer, skin cancer, blood tumor (e.g., adult T cell leukemia, chronic myeloid leukemia, malignant lymphoma and the like) and the like); various infections, for example, viral disease (e.g., viral hepatitis due to HEPATITIS B virus, HEPATITIS C virus, HEPATITIS D virus, herpes, acquired immunodeficiency syndrome (AIDS) and the like), bacterial infections (e.g., medicament resistance tuberculosis, atypical mycobacterial infection and the like), mycosis (e.g., candidosis and the like) and the like in mammals (e.g., mouse, cat, bovine, dog, horse, goat, monkey, human).

In addition, as long as the efficacy is not impaired, compound (1) and the like of the present invention can be used in combination with other medicaments, for example, existing anti-cancer agents, antiviral drugs, antibacterial drugs, antifungal drugs and the like. In this case, the period for administration is not limited and these agents may be administered to the subject simultaneously or in time intervals. The dose can be appropriately determined by taking into account the clinically adopted dose as a standard. The mixing ratio of the compound (1) and the like to the concomitant drug may be appropriately determined depending on the administration subject, administration route, target disease, conditions, combination, and the like.

Examples of the existing anticancer agents include chemotherapeutic drugs, hormone therapeutic drugs, immunotherapeutic drugs, and the like.

Examples of the chemotherapeutic drugs include alkylating drugs (e.g., Cyclophosphamide, Iphosphamide, Nimustine, Ranimustine, Carboquone, etc.), antimetabolic drugs (e.g., Methotrexate, 5-Fluorouracil, Tegafur, Carmofur, UFT, Doxyfluridine, Cytarabine, Enocitabine, Mercaptopurine, Mercaptopurine riboside, Thioguanine, etc.), anticancer antibiotics (e.g., Mytomicin, Adriamycin, Daunorubicin, Epirubicin, Pirarubicin, Idarubicin, Bleomycin, Peplomycin, Actinomycin, etc.), plant-derived antitumor agents (e.g., Vincristine, Vinblastine, Vindesine, Etoposide, Camptothecine, Irinotecan, etc.), Cisplatin, Carboplatin, Nedaplatin, Paclitaxel, Docetaxel, Estramustine, and the like.

Examples of the hormone therapeutics include adrenocortical hormones (e.g., Prednisolone, Prednisone, Dexamethasone, Cortisone acetate, etc.), estrogens (e.g., Estradiol, Ethynylestradiol, Fosfestrol, Clorotrianisene, etc.), antiestrogens (e.g., Epithiostanol, Mepitiostane, Tamoxifen, Clomiphene, etc.), luteinizing hormones (e.g., Hydroxyprogesterone caproate, Dydrogesterone, Medroxyprogesterone, Norethysterone, Norethindrone, etc.), LHRH derivatives (e.g., Leuprorelin acetate, etc.) and the like.

Examples of the immunotherapeutic drugs include microorganism- or bacterium-derived components (e.g., muramyl dipeptide derivatives, Picibanil, etc.), polysaccharides having an immunopotentiating activity (e.g., lentinan, schizophyllan, krestin, etc.), genetically engineered cytokines (e.g., interferons, interleukin 2 (IL-2), interleukin 12 (IL-12), tumor necrosis factor (TNF), etc.), colony stimulating agents (e.g., granulocyte colony stimulating factor, erythropoietin, etc.) and the like.

Examples of the antiviral drug include nucleic acid synthesis inhibitory antiviral drugs (e.g., acyclovir, ganciclovir, vidarabine, foscarnet, zidovudine, lamivudine, didanosine, etc.), intracellular invasion inhibitory antiviral drugs (e.g., amantadine, zanamivir, oseltamivir etc.), host phylaxis ability enhancing antiviral drugs (e.g., interferon, isoprinosine, etc.), and the like.

Examples of the antibacterial drug include penicillin antibiotics (e.g., sawacillin, pasetocin, yamacillin, bacacil, viccillin, pentrex etc.), cephem antibiotics (e.g., keflex, kefral, cefzon, tomiron, cefspan, pansporin etc.), macrolide antibiotics (e.g., erythrosine, clarith, klaricid, rulid, josamycin etc.), tetracycline antibiotics (e.g., minomycin, vibramycin, hydramycin, ledermycin etc.), fosfomycin antibiotics (e.g., fosmicin, eukocin etc.), aminoglycoside antibiotics (e.g., kanamycin, etc.), new quinolone antibacterial drug (e.g., cravat, tarivid, baccidal, tosuxacin, ozex etc.), and the like.

Examples of the antifungal agent include polyene antifungal drugs (e.g., trichomycin, amphotericin B, nystatin, etc.), imidazole antifungal drugs (e.g., econazole, miconazole, clotrimazole, etc), triazole antifungal drugs (e.g., fluconazole, itoraconazole, etc.), allylamine antifungal drugs (e.g., butenafine, terbinafine hydrochloride, etc.), flucytosine (5-FC) antifungal drugs (e.g., flucytosine, etc.), and the like.

When compound (1) and the like relating to the present invention is administered to a human, it can be safely administered orally or parenterally, as is or after being blended with a pharmacologically acceptable carrier, excipient, diluent and the like, in the form of pharmaceutical compositions such as oral preparations (e.g., powders, granules, tablets, capsules), parenteral preparations (e.g., injections), and suppositories (e.g., rectal suppositories, vaginal suppositories). These preparations can be produced by conventionally known methods.

Examples of the injection include subcutaneous injections, intravenous injections, intramuscular injections, intraperitoneal injections, drip infusions and the like. An injection can be prepared as an aqueous injection by treating compound (1) and the like in the presence of a solubilizer (e.g., β-cyclodextrins), a dispersing agent (e.g., carboxymethylcellulose, sodium alginate), a preservative (e.g., methylparaben, propylparaben, benzyl alcohol, chlorobutanol), an isotonizing agent (e.g., sodium chloride, glycerol, sorbitol, glucose) and the like by a conventional method. An injection can also be prepared as an oily injection by dissolving, suspending or emulsifying compound (1) and the like in a vegetable oil (e.g., olive oil, sesame oil, peanut oil, cottonseed oil, corn oil), propylene glycol and the like.

An oral preparation can also be produced by adding to compound (1) and the like, for example, an excipient (e.g., lactose, saccharose, starch), a disintegrant (e.g., starch, calcium carbonate), a binder (e.g., starch, gum arabic, carboxymethylcellulose, polyvinylpyrrolidone, hydroxypropylcellulose) or a lubricant (e.g., talc, magnesium stearate, polyethyleneglycol) and the like as appropriate, compression-molding the mixture, and then, as required, coating the mixture with hydroxypropylmethylcellulose and the like. A suppository can be produced by blending compound (1) and the like with a non-irritant excipient (e.g., polyethylene glycol, glycerides of higher fatty acids).

The dose of compound (1) and the like varies depending on the age, body weight, symptoms, dosage form, method of administration, duration of administration and the like; for example, for a patient (adult, weighing about 60 kg), a daily dose of 0.1 to 1 mg/kg, preferably 0.5 to 1 mg/kg, more preferably 0.8 to 1 mg/kg, is administered orally or parenterally in a single to several divided portions.

EXAMPLES

The present invention is explained in detail by referring to the following Examples, which are not to be construed as limitative.

Example 1

Synthesis of Compound F

The synthesis processes are as described in the following scheme.

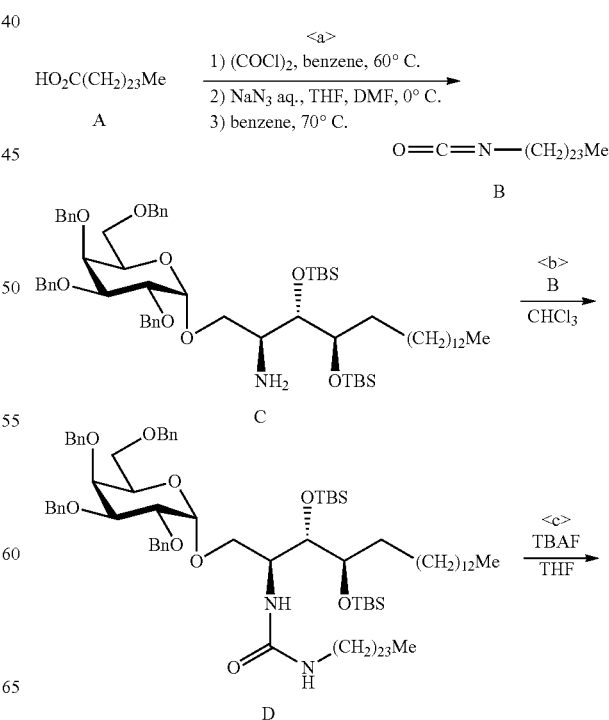

-continued

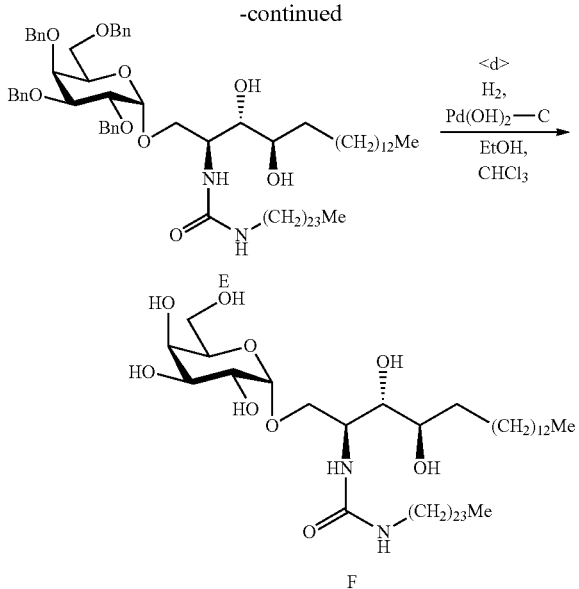

<a> Synthesis of Compound B

A suspension of commercially available compound A (310 mg, 0.810 mmol) in anhydrous benzene (5 mL) was heated to 60° C. to allow dissolution. To the obtained solution was added oxalyl chloride (1.0 mL, 12 mmol) at 60° C. The reaction mixture was stirred at 60° C. for 2 hr and concentrated under reduced pressure to give an acid chloride.

The obtained acid chloride was dissolved in a mixed solvent of tetrahydrofuran (5 ml) and N,N-dimethylformamide (2 mL), and cooled to 0° C. A solution of sodium azide (107 mg, 1.65 mmol) in water (1 mL) was slowly added at 0° C., and the mixture was stirred at 0° C. for 2 hr. The reaction mixture was diluted with benzene and washed successively with water and saturated brine, and the organic layer was dried over anhydrous sodium sulfate. After filtration, the filtrate was stirred at 70° C. for 2 hr, concentrated under reduced pressure, and the solvent was evaporated. The residue was diluted with hexane, and the insoluble material was removed by filtration. The filtrate was concentrated under reduced pressure to give compound B (187 mg, 61%) as a colorless solid. The obtained compound B was used for the next reaction without further purification.

IR (film): $\nu_{max}$=2335 (s, N=C=O) cm$^{-1}$.

<b> Synthesis of Compound D

Compound C was prepared according to the method described in Bioorganic & Medicinal Chemistry, 2008, 16, 8896-8906. To a solution of compound C (211 mg, 0.197 mmol) in chloroform (3 mL) was added a solution of compound B (187 mg, 0.493 mmol) in chloroform (2 mL) under ice-cooling. The reaction mixture was stirred at room temperature overnight, and water was added. The mixture was diluted with ethyl acetate, and the separated organic layer was washed successively with water, saturated aqueous sodium hydrogen carbonate solution and saturated brine, and dried over anhydrous magnesium sulfate. After filtration, the filtrate was concentrated under reduced pressure, and the solvent was evaporated. The residue was purified by silica gel column chromatography (20 g, hexane:ethyl acetate-10:1) to give compound D (276 mg, 97%) as a colorless oil.

$n_D^{25}$=1.5010.

$[\alpha]_D^{26}$=+26.1 (c=1.33, CHCl$_3$).

IR (film): $\nu_{max}$=3380 (m, NH), 1680 (m, C=O), 1660 (m, C=O), 1540 (m), 1255 (m, t-Bu, Si-Me), 1100 (br s, C—O), 1060 (br s, C—O), 835 (s), 755 (br s), 700 (m) cm$^{-1}$.

$^1$H-NMR (500 MHz, CDCl$_3$): δ=7.38-7.23 (20H, m), 4.93 (1H, d, J=12 Hz), 4.89 (1H, d, J=6.5 Hz), 4.83 (1H, d, J=4.0 Hz), 4.80 (1H, d, J=12 Hz), 4.79 (1H, d, J=12 Hz), 4.72 (1H, d, J=12 Hz), 4.63 (1H, d, J=12 Hz), 4.55 (1H, d, J=12 Hz), 4.46 (1H, d, J=12 Hz), 4.43 (1H, d, J=12 Hz), 4.34 (1H, br s), 4.04 (1H, dd, J=9.5, 3.5 Hz), 3.97 (1H, t, J=6.0 Hz), 3.95 (1H, dd, J=11, 6.5 Hz), 3.90 (1H, dd, J=11, 3.5 Hz), 3.89 (1H, s), 3.87 (1H, dd, J=6.0, 1.5 Hz), 3.81 (1H, dd, J=11, 3.5 Hz), 3.81-3.75 (1H, m), 3.72 (1H, dt, J=6.0, 1.5 Hz), 3.57 (1H, dd, J=9.5, 6.5 Hz), 3.38 (1H, dd, J=9.5, 6.0 Hz), 2.98-2.87 (2H, m), 1.69 (2H, br s), 1.50 (2H, br q, J=7.0 Hz), 1.44-1.16 (66H, m), 0.90 (9H, s), 0.884 (9H, s), 0.879 (6H, t, J=7.0 Hz), 0.08 (3H, s), 0.06 (3H, s), 0.05 (3H, s), 0.03 (3H, s) ppm.

$^{13}$C-NMR (126 MHz, CDCl$_3$): δ=158.4, 138.7, 138.52, 138.48, 137.8, 128.5, 128.38, 128.37, 128.2, 127.9, 127.84, 127.83, 127.7, 127.6, 127.5, 127.4, 100.5, 78.9, 76.9, 76.4, 75.14, 75.12, 74.7, 73.6, 73.4, 73.1, 71.2, 70.0, 69.7, 52.5, 40.2, 32.7, 31.92, 31.91, 30.4, 30.0, 29.72, 29.70, 29.69, 29.66, 29.65, 29.42, 29.36, 29.35, 26.9, 26.2, 26.1, 26.0, 22.7, 18.4, 18.2, 14.1, -3.76, -3.84, -4.7, -4.91 ppm.

HR-ESIMS: Calcd for [M+H]$^+$ (C$_{89}$H$_{151}$N$_2$O$_9$Si$_2$): 1448.0953; found: 1448.0943.

<c> Synthesis of Compound E

To a solution of compound D (174 mg, 0.120 mmol) in tetrahydrofuran (5 mL) was added a solution (1.0 M, 1.2 mL, 1.2 mmol) of tetrabutylammonium fluoride in tetrahydrofuran at room temperature. The reaction mixture was stirred at room temperature overnight, and water was added. The mixture was diluted with ethyl acetate, and the separated organic layer was washed successively with water and saturated brine, and dried over anhydrous magnesium sulfate. After filtration, the filtrate was concentrated under reduced pressure and the solvent was evaporated. The residue was purified by, silica gel column chromatography (20 g, hexane:ethyl acetate=3:2) to give compound E (136 mg, 93%) as a white solid.

$[\alpha]_D^{22}$=+23.2 (c=1.10, CHCl$_3$).

IR (KBr): ν=3360 (br s, OH, NH), 1630 (br s, C=O), 1570 (br s), 1110 (br s, C—O), 1040 (br s, C—O), 730 (br s), 695 (s) cm$^{-1}$.

$^1$H-NMR (500 MHz, CDCl$_3$): δ=7.38-7.24 (20H, m), 5.32 (1H, d, J=7.5 Hz), 4.92 (1H, d, J=12 Hz), 4.85 (1H, d, J=12 Hz), 4.83 (1H, d, J=4.0 Hz), 4.78 (1H, d, J=12 Hz), 4.73 (1H, d, J=12 Hz), 4.66 (1H, d, J=12 Hz), 4.56 (1H, d, J=12 Hz), 4.48 (1H, d, J=12 Hz), 4.39 (1H, d, J=12 Hz), 4.35 (1H, t, J=5.5 Hz), 4.17 (1H, d, J=7.0 Hz), 4.04 (1H, dd, J=10, 4.0 Hz), 3.99-3.92 (4H, m), 3.88-3.83 (2H, m), 3.54 (1H, dd, J=9.5, 6.5 Hz), 3.55-3.49 (2H, m), 3.45 (1H, dd, J=9.5, 6.0 Hz), 3.08-2.97 (2H, m), 2.39 (1H, d, J=5.0 Hz), 1.66-1.58 (1H, m), 1.52-1.44 (1H, m), 1.42-1.20 (68H, m), 0.88 (6H, t, J=7.0 Hz) ppm.

$^{13}$C-NMR (126 MHz, CDCl$_3$): δ=158.3, 138.4, 138.3, 138.0, 137.3, 128.51, 128.49, 128.4, 128.26, 128.25, 128.1, 128.0, 127.9, 127.7, 127.6, 127.4, 99.2, 79.1, 76.4, 76.2, 74.7, 74.6, 74.0, 73.7, 73.3, 72.9, 70.4, 69.9, 69.5, 51.2, 40.5, 33.5, 31.9, 30.2, 29.74, 29.71, 29.70, 29.65, 29.64, 29.62, 29.37, 29.354, 29.347, 26.9, 26.0, 22.7, 14.1 ppm.

HR-ESIMS: Calcd for [M+H]$^+$ (C$_{77}$H$_{123}$N$_2$O$_9$): 1219.9223; found: 1219.9212.

<d> Synthesis of Compound F

Compound E (105 mg, 0.0861 mmol) was dissolved in a mixed solvent of ethanol (8 mL) and chloroform (2 mL), and palladium hydroxide-activated carbon (20%, wet, 40 mg) was added thereto at room temperature. The suspension was stirred overnight under a hydrogen atmosphere, and diluted with a mixed solvent (5:1) of chloroform and methanol. After filtration, the filtrate was concentrated under reduced pressure, and the solvent was evaporated. The residue was purified by silica gel column chromatography (10 g, chloroform: methanol=25:3) to give compound F (58 mg, 78%) as white powder.

$[\alpha]_D^{26}$=+46.5 (c=0.30, pyridine).

IR (KBr): $\nu_{max}$=3360 (br s, OH, NH), 1635 (br m, C=O), 1570 (br m), 1070 (br s, C—O) cm$^{-1}$.

$^1$H-NMR (500 MHz, pyridine-d$_5$): δ=6.79 (1H, t, J=6.0 Hz), 6.75 (1H, d, J=9.0 Hz), 6.44-5.90 (6H, m), 5.54 (1H, d, J=4.0 Hz), 5.09-5.04 (1H, m), 4.60 (1H, dd, J=9.5, 4.0 Hz), 4.58 (1H, dd, J=11, 5.0 Hz), 4.48 (1H, br d, J=4.0 Hz), 4.46-4.36 (3H, m), 4.34 (1H, dd, J=11, 5.0 Hz), 4.32 (1H, dd, J=9.5, 3.0 Hz), 4.28-4.23 (2H, m), 3.48 (1H, ddt, J=13, 7.5, 6.0 Hz), 3.40 (1H, ddt, J=13, 7.5, 6.0 Hz), 2.28-2.21 (1H, m), 1.91-1.78 (2H, m), 1.68-1.58 (1H, m), 1.55 (2H, quint., J=7.5 Hz), 1.44-1.16 (64H, m), 0.85 (6H, t, J=7.0 Hz) ppm.

$^{13}$C-NMR (126 MHz, pyridine-d$_5$): δ=159.5, 101.6, 77.4, 73.0, 72.8, 71.6, 70.9, 70.2, 69.7, 62.7, 51.9, 40.6, 34.7, 32.1, 31.0, 30.3, 30.1, 30.01, 30.00, 29.98, 29.96, 29.93, 29.91, 29.89, 29.7, 29.59, 29.58, 27.4, 26.5, 22.9, 14.3 ppm.

HR-ESIMS: Calcd for [M+H]$^+$ ($C_{49}H_{99}N_2O_9$): 859.7345; found: 859.7346.

Example 2

Synthesis of Compound G

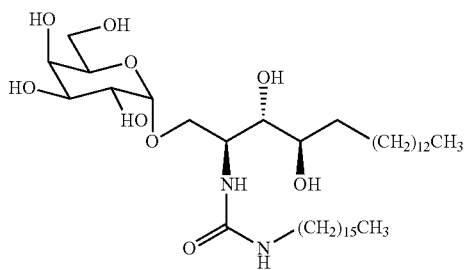

G

Compound G was synthesized in the same manner as in Example 1.

$[\alpha]_D^{26}$=+55.7 (c=0.30, pyridine).

IR (KBr): $\nu_{max}$=3320 (br s, OH, NH), 1630 (br s, C=O), 1570 (br s), 1070 (br s, C—O), 1030 (br s, C—O) cm$^{-1}$.

$^1$H-NMR (500 MHz, pyridine-d$_5$): δ=6.81 (1H, t, J=5.5 Hz), 6.79 (1H, d, J=9.5 Hz), 6.66-5.70 (6H, m), 5.54 (1H, d, J=4.0 Hz), 5.10-5.05 (1H, m), 4.61 (1H, dd, J=9.5, 3.5 Hz), 4.59 (1H, dd, J=11, 4.5 Hz), 4.48 (1H, d, J=3.0 Hz), 4.47-4.42 (2H, m), 4.41-4.33 (2H, m), 4.37 (1H, dd, J=11, 6.0 Hz), 4.28-4.23 (2H, m), 3.48 (1H, ddt, J=13, 7.5, 5.5 Hz), 3.40 (1H, ddt, J=13, 7.5, 5.5 Hz), 2.28-2.21 (1H, m), 1.92-1.78 (2H, m), 1.66-1.56 (1H, m), 1.55 (2H, quint., J=7.5 Hz), 1.43-1.15 (48H, m), 0.84 (6H, t, J=7.0 Hz) ppm.

$^{13}$C-NMR (126 MHz, pyridine-d$_5$): δ=159.5, 101.6, 77.4, 73.0, 72.8, 71.6, 70.9, 70.2, 69.7, 62.7, 52.0, 40.6, 34.7, 32.1, 31.0, 30.4, 30.1, 30.01, 29.98, 29.92, 29.91, 29.7, 29.6, 27.4, 26.5, 22.9, 14.3 ppm.

HR-ESIMS: Calcd for [M+H]$^+$ ($C_{41}H_{83}N_2O_9$): 747.6093; found: 747.6091.

Example 3

Synthesis of Compound H

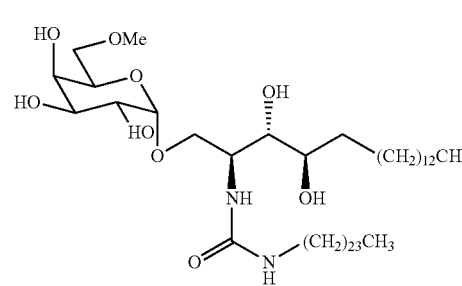

H

Compound H was synthesized in the same manner as in Example 1.

$[\alpha]_D^{25}$=+50.2 (c=0.29, pyridine).

IR (KBr): $\nu_{max}$=3340 (br s, OH, NH), 1640 (br s, C=O), 1570 (br s), 1070 (br s, C—O), 1035 (br s, C—O) cm$^{-1}$.

$^1$H-NMR (500 MHz, pyridine-d$_5$): δ=7.04 (1H, br s), 6.77 (1H, t, J=5.5 Hz), 6.68 (1H, d, J=9.0 Hz), 6.63 (1H, br s), 6.29 (2H, br s), 6.01 (1H, d, J=5.5 Hz), 5.51 (1H, d, J=4.0 Hz), 5.09 (1H, dq, J=8.5, 4.0 Hz), 4.60 (1H, dd, J=11, 5.5 Hz), 4.57 (1H, dd, J=10, 4.0 Hz), 4.42-4.36 (2H, m), 4.33-4.21 (4H, m), 3.95 (1H, dd, J=10, 5.5 Hz), 3.90 (1H, dd, J=10, 7.0 Hz), 3.48 (1H, ddt, J=13, 7.0, 5.5 Hz), 3.40 (1H, ddt, J=13, 7.0, 5.5 Hz), 3.32 (3H, s), 2.29-2.21 (1H, m), 1.92-1.78 (2H, m), 1.67-1.58 (1H, m), 1.56 (2H, quint., J=7.0 Hz), 1.44-1.17 (64H, m), 0.84 (6H, t, J=7.0 Hz) ppm.

$^{13}$C-NMR (126 MHz, pyridine-d$_5$): δ=159.3, 101.5, 77.3, 72.9, 72.8, 71.3, 70.7, 70.6, 70.0, 69.6, 58.8, 51.8, 40.6, 34.8, 32.1, 31.0, 30.3, 30.1, 30.01, 30.00, 29.98, 29.96, 29.94, 29.93, 29.91, 29.90, 29.7, 29.60, 29.59, 27.4, 26.4, 22.9, 14.3 ppm.

HR-ESIMS: Calcd for [M+H]$^+$ ($C_{50}H_{101}N_2O_9$): 873.7502; found: 873.7503.

Example 4

Synthesis of Compound I

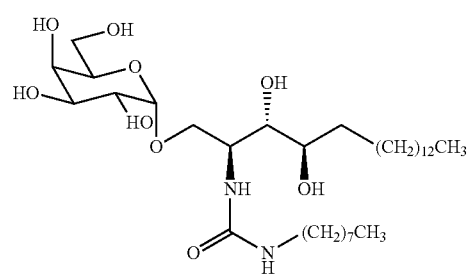

I

Compound I was synthesized in the same manner as in Example 1.

$[\alpha]_D^{22}$=+56.5 (c=0.32, pyridine).

IR (KBr): $\nu_{max}$=3360 (br s, OH, NH), 1640 (br s, C=O), 1570 (br s, C=O), 1070 (br s, C—O) cm$^{-1}$.

$^1$H-NMR (500 MHz, pyridine-$d_5$): δ=7.02 (1H, br s), 6.80 (1H, t, J=6.0 Hz), 6.76 (1H, d, J=9.0 Hz), 6.63 (2H, br s), 6.37 (1H, br s), 6.34 (1H, br s), 6.05 (1H, br s), 5.55 (1H, d, J=4.0 Hz), 5.15-5.06 (1H, m), 4.61 (1H, dd, J=8.0, 4.0 Hz), 4.59 (1H, dd, J=10, 4.5 Hz), 4.49 (1H, d, J=3.0 Hz), 4.47-4.35 (3H, m), 4.37 (1H, dd, J=10, 5.5 Hz), 4.33 (1H, dd, J=10, 3.0 Hz), 4.30-4.22 (2H, m), 3.46 (1H, ddt, J=13, 7.0, 6.0 Hz), 3.39 (1H, ddt, J=13, 7.0, 6.0 Hz), 2.30-2.22 (1H, m), 1.91-1.78 (2H, m), 1.66-1.56 (1H, m), 1.52 (2H, quint., J=7.0 Hz), 1.42-1.08 (32H, m), 0.84 (3H, t, J=7.0 Hz), 0.79 (3H, t, J=7.0 Hz) ppm.

$^{13}$C-NMR (126 MHz, pyridine-$d_5$): δ=159.5, 101.6, 77.4, 73.0, 72.8, 71.6, 70.9, 70.2, 69.7, 62.7, 52.0, 40.6, 34.7, 32.1, 32.0, 31.0, 30.4, 30.1, 30.01, 30.00, 29.97, 29.96, 29.90, 29.59, 29.58, 29.5, 27.3, 26.5, 22.9, 22.8, 14.3, 14.2 ppm.

HR-ESIMS: Calcd for [M+H]$^+$ ($C_{33}H_{67}N_2O_9$): 635.4841; found: 635.4841.

Example 5

Synthesis of Compound J

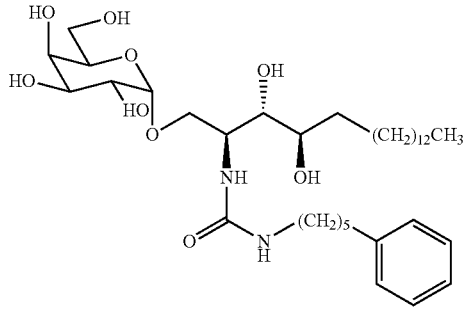

Compound J was synthesized in the same manner as in Example 1.

[α]$_D^{25}$=+58.4 (c=0.31, pyridine).

IR (KBr): $ν_{max}$=3360 (br s, OH, NH), 1640 (br s, C=O), 1570 (br s, C=O), 1070 (br s, C—O), 700 (m) cm$^{-1}$.

$^1$H-NMR (500 MHz, pyridine-$d_5$): δ=7.29 (2H, ddt, J=7.5, 1.5, 1.0 Hz), 7.21-7.14 (3H, m), 7.02 (1H, br s), 6.80 (1H, t, J=5.5 Hz), 6.75 (1H, d, J=9.0 Hz), 6.34 (2H, br s), 6.37 (1H, br s), 6.34 (1H, br s), 6.07 (1H, br s), 5.56 (1H, d, J=3.5 Hz), 5.11-5.06 (1H, m), 4.62 (1H, dd, J=10, 4.0 Hz), 4.60 (1H, dd, J=10, 5.0 Hz), 4.49 (1H, d, J=2.0), 4.47-4.36 (3H, m), 4.38 (1H, dd, J=10, 6.0 Hz), 4.33 (1H, dd, J=10, 4.0 Hz), 4.30-4.22 (2H, m), 3.42 (1H, ddt, J=13, 7.0, 5.5 Hz), 3.36 (1H, ddt, J=13, 7.0, 5.5 Hz), 2.45 (2H, t, J=7.0 Hz), 2.30-2.22 (1H, m), 1.91-1.78 (2H, m), 1.66-1.56 (1H, m), 1.52 (2H, quint., J=7.0 Hz), 1.47 (2H, quint., J=7.0 Hz), 1.42-1.17 (24H, m), 0.84 (3H, t, J=7.0 Hz) ppm.

$^{13}$C-NMR (126 MHz, pyridine-$d_5$): δ=159.4, 143.0, 128.8, 128.6, 126.0, 101.6, 77.4, 73.0, 72.7, 71.5, 70.9, 70.2, 69.6, 62.6, 51.9, 40.4, 36.0, 34.7, 32.1, 31.5, 30.8, 30.3, 30.1, 29.99, 29.98, 29.95, 29.94, 29.88, 29.6, 26.9, 26.4, 22.9, 14.2 ppm.

HR-ESIMS: Calcd for [M+H]$^+$ ($C_{36}H_{65}N_2O_9$): 669.4685; found: 669.4685.

Experimental Example 1

Influence of Synthetic Glycolipid on Cytokine Production of NKT Cells

A solution of each of α-GalCer (KRN7000), compound F and compound H in dimethyl sulfoxide (DMSO) was prepared at a concentration of 1 mg/mL. The above-mentioned DMSO solution was diluted with saline (manufactured by Otsuka Pharmaceutical Co., Ltd.) containing 0.5% tween 20 (Bio-Rad) such that the dose became 100 μg/kg body weight when 200 μL per mouse was administered from the tail vein.

The prepared solutions (200 μL) of compounds F and H were respectively injected to C57BL/6 mice (5 mice per group) from the tail vein. As a control substance, α-GalCer (KRN7000) was used, and a solution (200 μL) of α-GalCer (KRN7000) prepared in the same manner such that the dose became 100 μg/kg body weight was injected into the tail vein. The group administered with saline (200 μL) containing 0.5% tween 20 (medium) was used as a negative control. The blood (80 μL) immediately before administration and after administration (after lapse of the time indicated in FIGS. 1-3) was collected from the orbital sinus and plasma was prepared.

The IFN-γ content of the plasma before administration and after administration (after lapse of the time indicated in FIG. 1) was measured by Cytometric Bead Array system (BD Biosciences) which is one of the ELISA methods. The measurement results (mean) of the production amount of IFN-γ and the standard deviation thereof (STDEV) are shown in FIG. 1.

Figure 2:
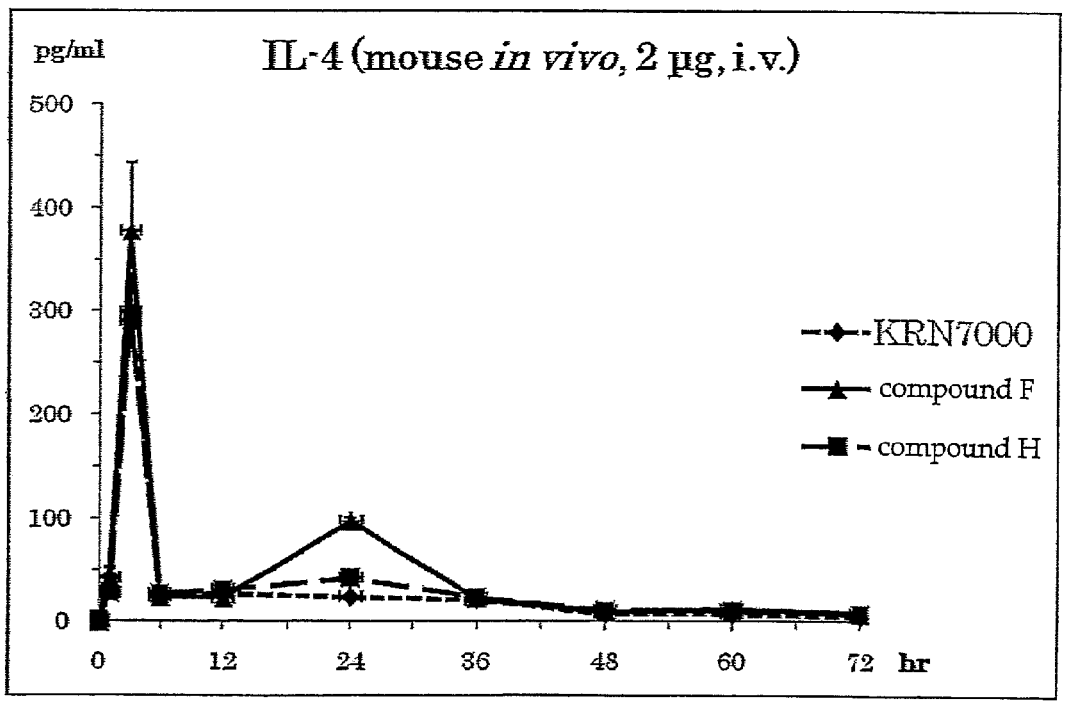
FIG. 2 shows IL-4 concentration in mouse plasma after lapse of indicated time after administration of a synthetic glycolipid to mice in vivo (Experimental Example 1).

The IL-4 content of the plasma before administration and after administration (after lapse of the time indicated in FIG. 2) was measured by Cytometric Bead Array system (BD Biosciences) which is one of the ELISA methods. The measurement results (mean) of the production amount of IL-4 and the standard deviation thereof (STDEV) are shown in FIG. 2.

Figure 3:
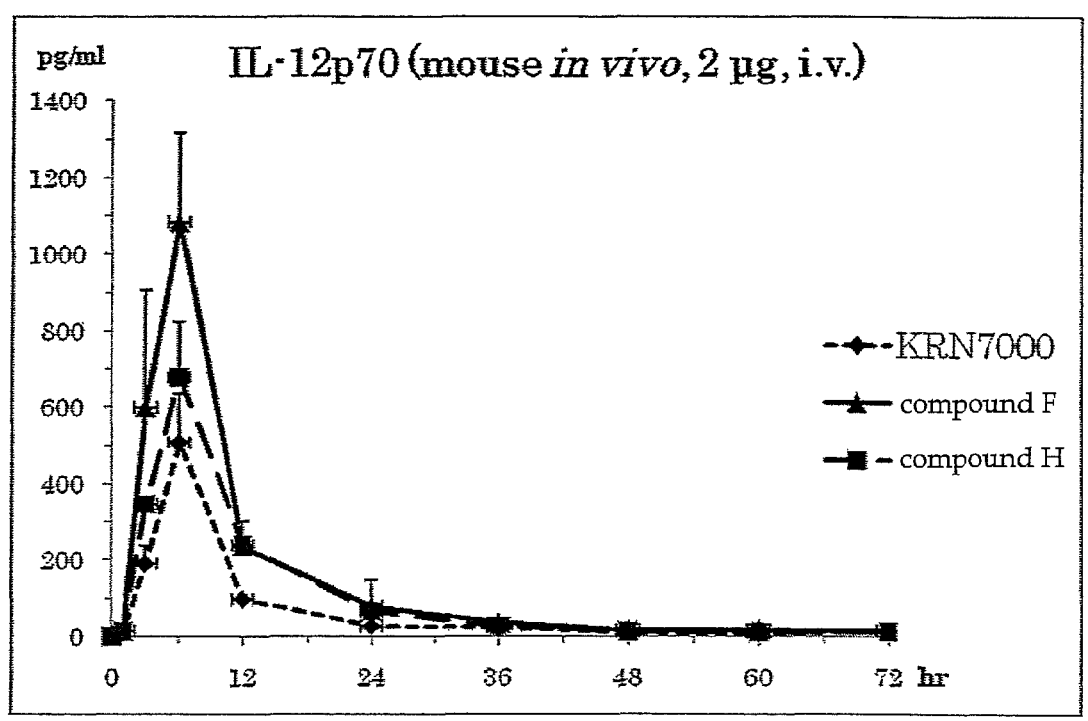
FIG. 3 shows IL-12 concentration in mouse plasma after lapse of indicated time after administration of a synthetic glycolipid to mice in vivo (Experimental Example 1).

The IL-12 content of the plasma before administration and after administration (after lapse of the time indicated in FIG. 3) was measured by Cytometric Bead Array system (BD Biosciences) which is one of the ELISA methods. The measurement results (mean) of the production amount of IL-12 and the standard deviation thereof (STDEV) are shown in FIG. 3.

From the above-mentioned results, compounds F and H selectively induced IFN-γ production in larger amounts than α-GalCer (KRN7000). That is, conversion of the amide bond of α-GalCer (KRN7000) to an urea bond resulted in the development of a novel compound capable of inducing cytokine production of mostly IFN-γ.

INDUSTRIAL APPLICABILITY

The present invention provides a production method of a medicament effective for the treatment of cancer or infection and use thereof.

This application is based on a patent application No. 2010-24859 filed in Japan, the contents of which are incorporated in full herein.

The invention claimed is:

1. A compound represented by the formula (1) or a salt thereof:

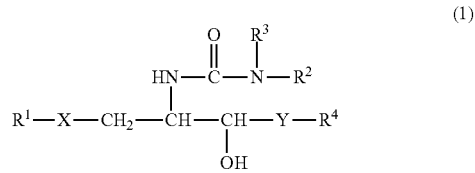

wherein R$^1$ is an aldopyranose residue wherein the 6-hydroxyl group is optionally alkylated, R$^2$ is a $C_{1-26}$ hydrocarbon group optionally having substituent(s), R$^3$ is a hydrogen atom or a $C_{1-26}$ hydrocarbon group optionally having substituent(s), $R^4$ is a $C_{1-21}$ hydrocarbon group optionally having substituent(s), X is an oxygen atom or —$CH_2$—, and Y is —$CH_2$—, —CH(OH)— or —CH=CH—.

2. The compound according to claim 1, wherein $R^1$ is α-D-galactopyranosyl, or a salt thereof.

3. The compound according to claim 1, wherein $R^2$ is a $C_{1-26}$ aliphatic hydrocarbon group optionally having substituent(s), and $R^3$ is a hydrogen atom, or a salt thereof.

4. The compound according claim 1, wherein $R^4$ is a $C_{1-21}$ alkyl group optionally having substituent(s), or a salt thereof.

5. The compound according claim 1, wherein X is an oxygen atom, or a salt thereof.

6. The compound according to claim 1, wherein Y is —CH(OH)—, or a salt thereof.

7. A compound represented by the formula (2) or a salt thereof:

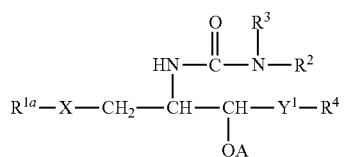

(2)

wherein $R^{1a}$ is an aldopyranose residue wherein the 6-hydroxyl group is optionally alkylated and the hydroxyl groups are protected, $R^2$ is a $C_{1-26}$ hydrocarbon group optionally having substituent(s), $R^3$ is a hydrogen atom or a $C_{1-26}$ hydrocarbon group optionally having substituent(s), $R^4$ is a $C_{1-21}$ hydrocarbon group optionally having substituent(s), X is an oxygen atom or —$CH_2$—, $Y^1$ is —$CH_2$—, —CH(OA)- or —CH=CH—, and A is a hydrogen atom or a hydroxyl-protecting group.

8. A pharmaceutical composition comprising (a) a compound according to claim 1 or a salt thereof, and (b) a pharmacologically acceptable carrier.

9. A method for the treatment of cancer, comprising administering an effective amount of a compound according to claim 1 or a salt thereof to a mammal, thereby treating cancer in the mammal.

10. A method of activating NKT cell, comprising administering an effective amount of a compound according to claim 1 or a salt thereof to a mammal, thereby activating NKT cell in the mammal.

11. A method of inducing selective IFN-γ production, comprising administering an effective amount of a compound according to claim 1 or a salt thereof to a mammal, thereby inducing selective IFN-γ production in the mammal.

12. A method for the treatment of infection, comprising administering an effective amount of a compound according to claim 1 or a salt thereof to a mammal, thereby treating infection in the mammal.

13. A method of producing a compound represented by the formula (1) or a salt thereof, comprising the steps (a) to (c):

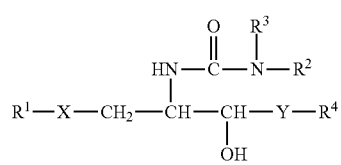

(1)

wherein $R^1$ is an aldopyranose residue wherein the 6-hydroxyl group is optionally alkylated, $R^2$ is a $C_{1-26}$ hydrocarbon group optionally having substituent(s), $R^3$ is a hydrogen atom or a $C_{1-26}$ hydrocarbon group optionally having substituent(s), $R^4$ is a $C_{1-21}$ hydrocarbon group optionally having substituent(s), X is an oxygen atom or —$CH_2$—, and Y is —$CH_2$—, —CH(OH)— or —CH=CH—, (a) reacting a compound represented by the formula (3):

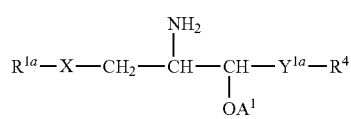

(3)

wherein $R^{1a}$ is an aldopyranose residue wherein the 6-hydroxyl group is optionally alkylated and the hydroxyl groups are protected, $R^4$ is a $C_{1-21}$ hydrocarbon group optionally having substituent(s), X is an oxygen atom or —$CH_2$—, and $Y^{1a}$ is —$CH_2$—, —CH($OA^1$)- or —CH=CH—, and $A^1$ is a hydroxyl-protecting group, or a salt thereof, with a compound represented by the formula (4) or (5):

(4)

(5)

wherein $R^2$ is a $C_{1-26}$ hydrocarbon group optionally having substituent(s), $R^3$ is a hydrogen atom or a $C_{1-26}$ hydrocarbon group optionally having substituent(s), and L is a leaving group to give a compound represented by the formula (2'):

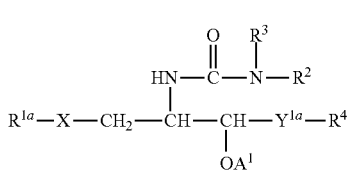

(2')

wherein each symbol is as defined above, or a salt thereof;

(b) deprotecting $A^1$ in a compound represented by the formula (2') or a salt thereof to give a compound represented by the formula (2"):

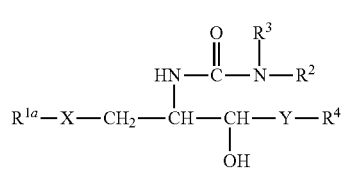

(2")

wherein each symbol is as defined above, or a salt thereof; and (c) removing the hydroxyl-protecting group at $R^{1a}$ of the compound represented by the formula (2") or a salt thereof to give a compound represented by the formula (1) or a salt thereof.

* * * * *